(12) United States Patent
Greenhalgh et al.

(10) Patent No.: US 12,280,202 B2
(45) Date of Patent: Apr. 22, 2025

(54) ROLLING SURGICAL DRAINS

(71) Applicant: Koko Medical, Inc., Exton, PA (US)

(72) Inventors: E. Skott Greenhalgh, Gladwyne, PA (US); Jason Keiser, Exton, PA (US)

(73) Assignee: Koko Medical, Inc., Exton, PA (US)

( * ) Notice: Subject to any disclaimer, the term of this patent is extended or adjusted under 35 U.S.C. 154(b) by 0 days.

(21) Appl. No.: 17/998,919

(22) PCT Filed: May 13, 2022

(86) PCT No.: PCT/US2022/029171
§ 371 (c)(1),
(2) Date: Nov. 15, 2022

(87) PCT Pub. No.: WO2022/241206
PCT Pub. Date: Nov. 17, 2022

(65) Prior Publication Data
US 2023/0241303 A1 Aug. 3, 2023

Related U.S. Application Data

(60) Provisional application No. 63/188,385, filed on May 13, 2021.

(51) Int. Cl.
*A61M 1/00* (2006.01)

(52) U.S. Cl.
CPC ............... *A61M 1/87* (2021.05); *A61M 1/915* (2021.05); *A61M 1/916* (2021.05)

(58) Field of Classification Search
CPC ........ A61M 1/87; A61M 1/915; A61M 1/916; A61M 39/0247; A61M 2039/0276
See application file for complete search history.

(56) References Cited

U.S. PATENT DOCUMENTS

| 5,505,710 | A  | * | 4/1996  | Dorsey, III | A61M 1/84 |
|           |    |   |         |             | 604/164.11 |
| 5,827,218 | A  | * | 10/1998 | Nguyen      | A61M 1/85 |
|           |    |   |         |             | 604/35 |
| 9,078,682 | B2 | * | 7/2015  | Lenker      | A61B 17/12118 |
| 9,550,014 | B2 |   | 1/2017  | Norred et al. | |
| 10,064,651 | B2 |   | 9/2018  | Norred et al. | |
| 10,722,255 | B2 |   | 7/2020  | Lenker et al. | |
| 10,765,847 | B1 |   | 9/2020  | Al-Jazaeri et al. | |
| 11,090,073 | B2 | * | 8/2021  | Tsukamoto   | A61B 17/22 |

(Continued)

FOREIGN PATENT DOCUMENTS

| WO | WO2021/016564 A1 | 1/2021 |
| WO | WO2022/140784 A1 | 6/2022 |

OTHER PUBLICATIONS

Kiefer et al.; U.S. Appl. No. 18/652,807 entitled "Rolling Surgical Drain with Angled Distal Tip" filed May 1, 2024.

*Primary Examiner* — Nicholas J. Weiss
*Assistant Examiner* — Peter Daniel Smith
(74) *Attorney, Agent, or Firm* — Shay Glenn LLP

(57) ABSTRACT

Described herein are negative pressure drains configured as "rolling" surgical drains including an invertible porous mesh having an expanded configuration so that negative pressure may be applied out of the invertible porous mesh to extend a uniform negative pressure within the body region being treated. The invertible porous mesh may then be withdrawn into the apparatus without significantly disrupting the tissue.

30 Claims, 19 Drawing Sheets

(56) References Cited

U.S. PATENT DOCUMENTS

| | | |
|---|---|---|
| 11,241,254 B2 | 2/2022 | Norred et al. |
| 2004/0006311 A1 | 1/2004 | Shchervinsky |
| 2007/0149996 A1* | 6/2007 | Coughlin .............. A61F 2/0105 606/200 |
| 2007/0249986 A1* | 10/2007 | Smego ................ A61M 1/3653 604/8 |
| 2012/0179144 A1* | 7/2012 | Carleo .............. A61M 25/0017 604/544 |
| 2015/0196380 A1 | 7/2015 | Berrada et al. |
| 2018/0055523 A1 | 3/2018 | Bair et al. |
| 2019/0105056 A1 | 4/2019 | Aboytes et al. |
| 2019/0117244 A1 | 4/2019 | Wallace et al. |
| 2020/0197032 A1 | 6/2020 | Wallace et al. |
| 2020/0330660 A1 | 10/2020 | Patel et al. |
| 2020/0352602 A1 | 11/2020 | Norred et al. |
| 2021/0068854 A1 | 3/2021 | Wallace et al. |
| 2021/0153883 A1 | 5/2021 | Casey et al. |
| 2021/0268157 A1 | 9/2021 | Ryan et al. |
| 2022/0022916 A1 | 1/2022 | Uchida et al. |

* cited by examiner

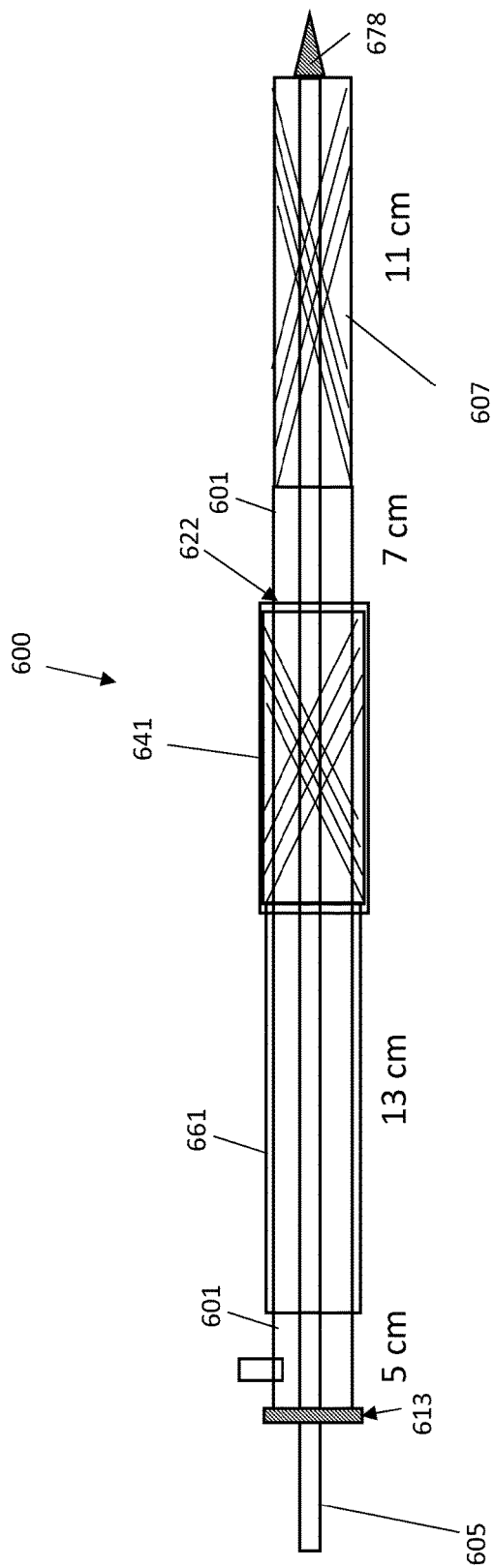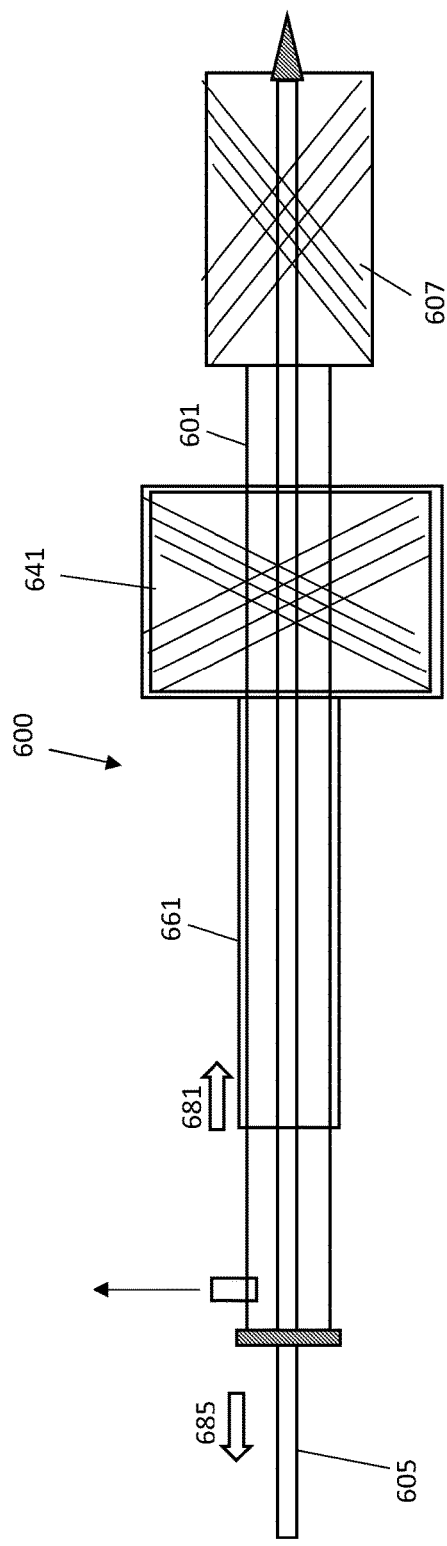
FIG. 6A
FIG. 6B

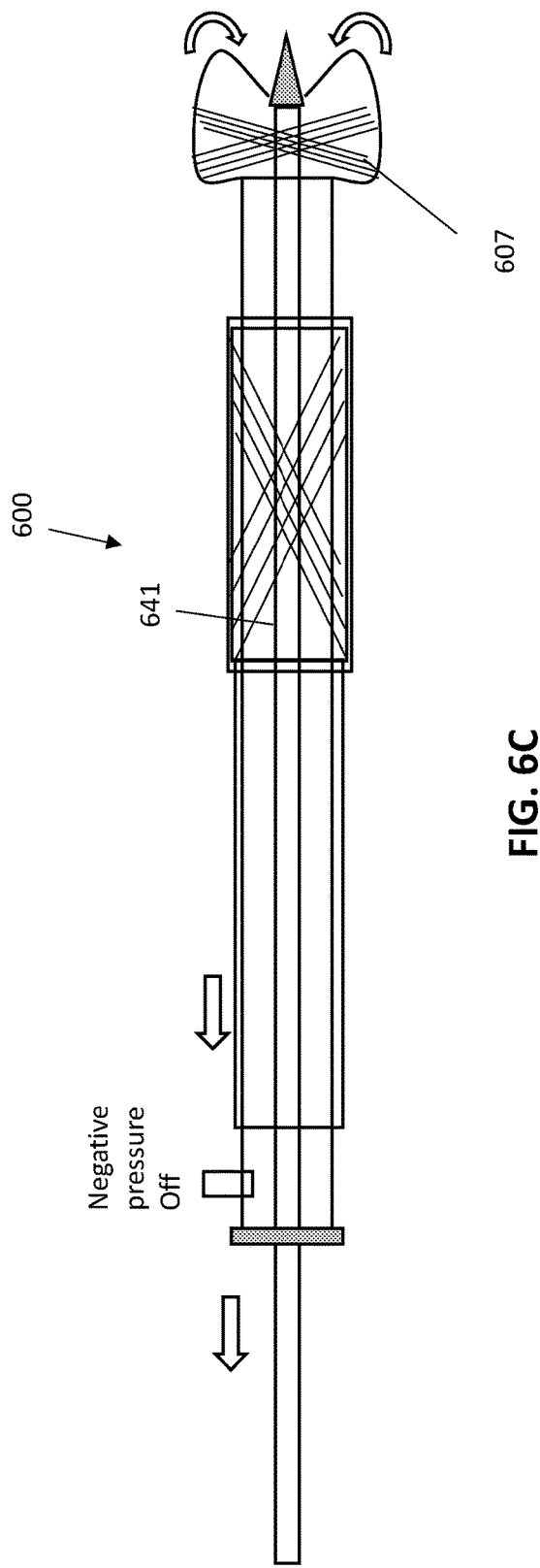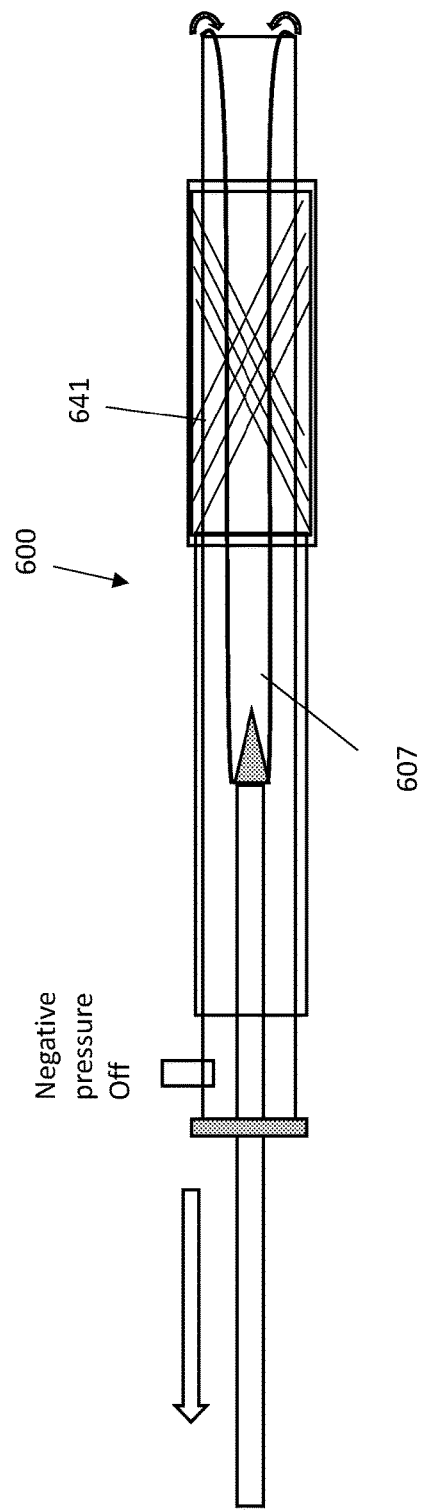
FIG. 6C
FIG. 6D

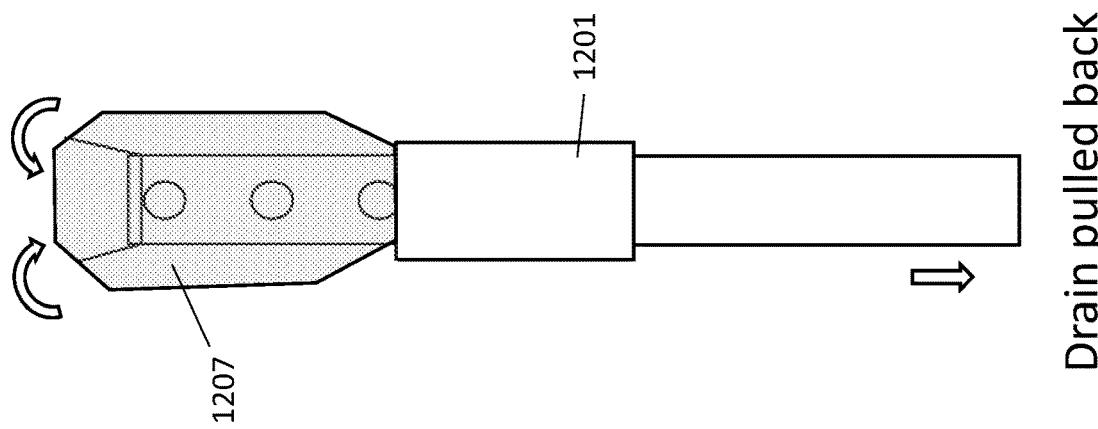
FIG. 12C Drain pulled back
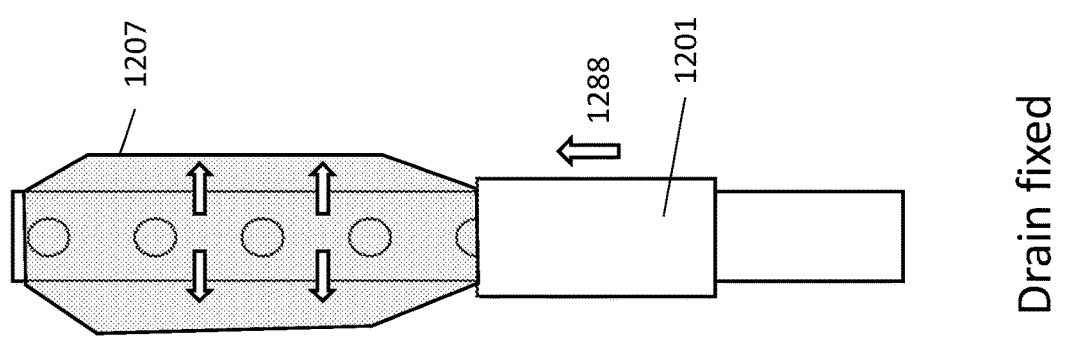
FIG. 12B Drain fixed
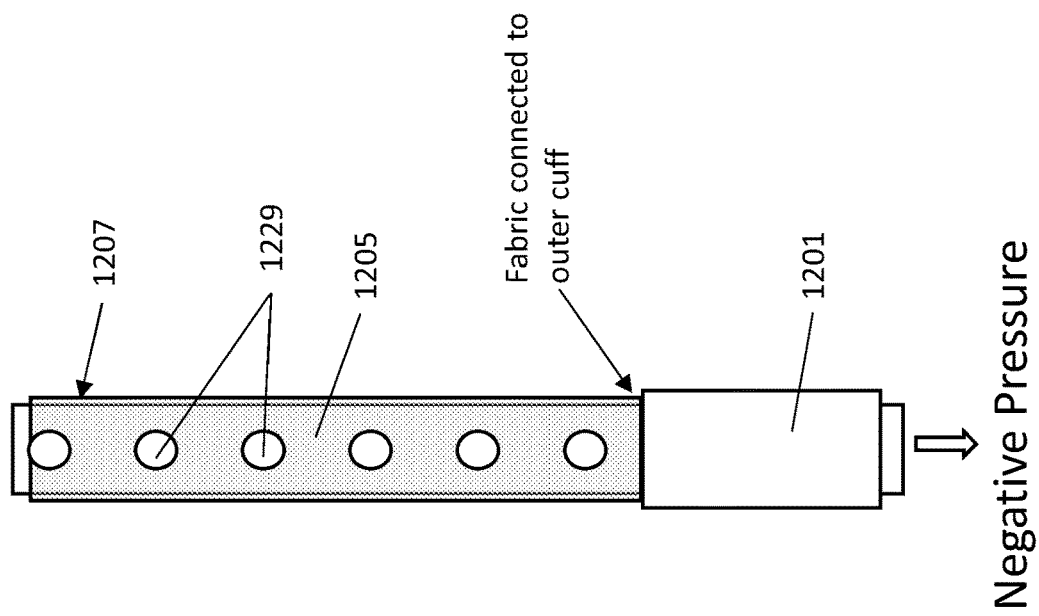
FIG. 12A Negative Pressure

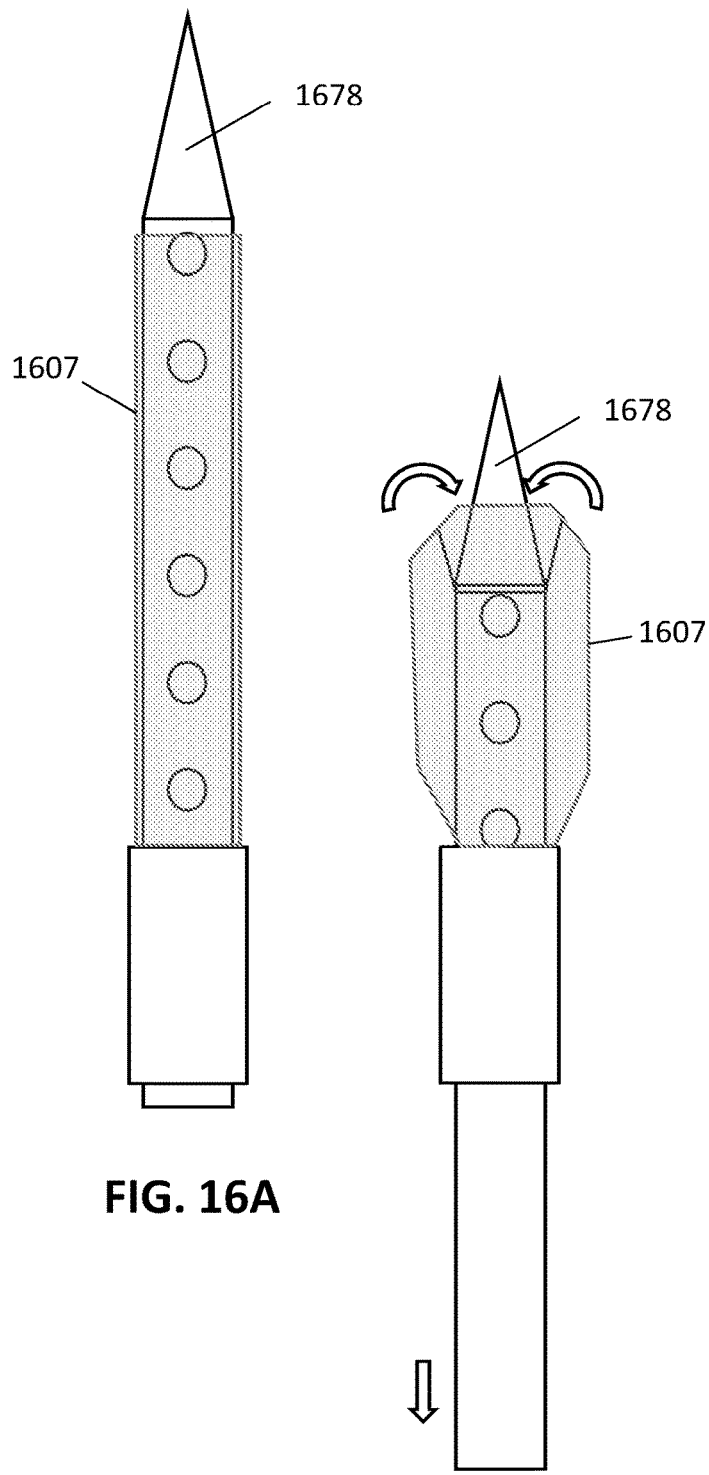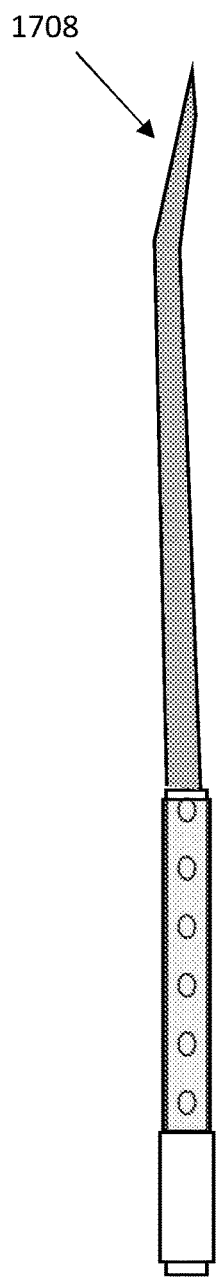
FIG. 16A
FIG. 16B
FIG. 17

```
┌─────────────────────────────────────────────────────────────┐
│ Position a distal end of an invertible porous mesh into a body │
│ region (e.g., wound, body cavity, tunnel, post-partum uterus, etc.) │
│                          1801                                │
└─────────────────────────────────────────────────────────────┘
                              │
                              ▼
┌─────────────────────────────────────────────────────────────┐
│    Expand the invertible porous mesh within the body region  │
│                          1803                                │
└─────────────────────────────────────────────────────────────┘
                              │
                              ▼
┌─────────────────────────────────────────────────────────────┐
│  Seal the invertible porous mesh within the body region (before or │
│        after expanding the invertible porous mesh)           │
│                          1805                                │
└─────────────────────────────────────────────────────────────┘
                              │
                              ▼
┌─────────────────────────────────────────────────────────────┐
│    Apply negative pressure from within the expanded invertible │
│  porous mesh to distribute the negative pressure within the sealed │
│                      body region                             │
│                          1807                                │
└─────────────────────────────────────────────────────────────┘
                              │
                              ▼
┌─────────────────────────────────────────────────────────────┐
│ Withdraw the invertible porous mesh by inverting and pulling the │
│  inverted invertible mesh into the lumen of the apparatus (e.g., a │
│              lumen of a first elongate member)               │
│                          1809                                │
└─────────────────────────────────────────────────────────────┘
                              │
                              ▼
┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
  Optionally maintain the negative pressure within the body region
                  for a period f time.
                          1811
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
```

FIG. 18A

ROLLING SURGICAL DRAINS

PRIORITY CLAIM

This patent application claims priority to U.S. provisional patent application No. 63/188,385, filed May 13, 2021, titled "ROLLING SURGICAL DRAINS AND METHODS FOR USE," and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Surgical drains are implants that allow removal of fluid (blood, pus, etc.) and/or gas from a wound or body cavity. This broadly includes nasogastric tubes, urinary catheters, vascular access ports, ventriculoperitoneal shunts, and negative pressure surgical drains. Negative pressure surgical drains are newer, active surgical drain, that are believed to provide advantages not realized with other types of surgical drains.

In general, surgical drains can help the healing process by removing inflammatory mediators, bacteria, foreign material, and necrotic tissue. Drains can relieve pressure that can impair perfusion or cause pain, thereby decreasing morbidity and reducing inflammation; they enable monitoring for potential complications by allowing easy sampling of fluid during healing; and they can be used to address complications associated with dead space. Active drains use intermittent or continuous negative pressure to pull fluid or gas from a wound or body cavity. Typically, passive drains are open systems and active drains are closed systems because they rely on negative pressure that is created by the drain.

Unfortunately, it is often difficult for negative pressure drains to provide uniform negative pressure within tissue cavities (both natural and those formed due to trauma), as soft tissue may collapse onto itself around the location(s) where pressure is applied, sealing off other regions from the pressure source. In addition, it may be difficult to remove the drain from tissue, particularly damaged and healing tissue, without causing further damage and disrupting nascent healing.

Negative pressure drains may be particularly helpful in treating postpartum uterine bleeding. Postpartum uterine bleeding can occur when the uterine muscles are unable to achieve adequate contraction after delivery to cut off the blood flow that formerly circulated in the utero-placental space. The condition for this lack of contraction is called atony (lack of tone). The uterine muscles typically cuts off the blood flow by contraction of the muscles to effectively pinch the arterial vessels that run through the tissue. In some cases, atony can result in arterial vessels that continue to bleed into the uterus (i.e., postpartum uterine bleeding). Postpartum hemorrhage, or excessive uterine blood loss after birth, is the leading cause of maternal death in the world. Inability to control postpartum bleeding can require a woman to receive multiple blood transfusions, and in severe cases, a full hysterectomy. Accordingly, it is desirable to control such postpartum bleeding. Current medical devices and surgical procedures have proven inadequate in reducing postpartum hemorrhage or the amount of blood lost, and/or are extremely invasive.

What is needed are negative pressure drains that can generate and sustain uniform regions of negative pressure within soft tissue, including, but not limited to the uterus, wounds and body cavities, without disrupting the apposition of tissue within the soft tissue and associated healing.

SUMMARY OF THE DISCLOSURE

The surgical drains and methods described herein provide negative pressure drains that can generate and sustain uniform regions of negative pressure within soft tissue. These apparatuses (devices, systems, drains, etc.) may be referred to as "rolling" surgical drains, and typically include a pair of coaxially arranged elongate members to which a distal invertible porous mesh is coupled. The apparatus is configured to apply suction through the invertible porous mesh. The invertible porous mesh may be compliant and may distribute the negative pressure (suction) within the soft tissue region being treated. The apparatus may include one or more integrated or separate occluders that may help seal off the soft tissue region so that the negative pressure may be sustained. The invertible porous mesh may be withdrawn from the soft tissue region by pulling it into the outer elongate member (e.g., pulling on the inner elongate member) so that it inverts over itself as it is withdrawn proximally. This inverting and rolling into itself is remarkably gentle, allowing the removal of the invertible porous mesh without disrupting the apposition and healing of the soft tissue.

These apparatuses may be used for any appropriate tissue, particularly soft tissue injuries in which draining and appropriate alignment of the tissue is desirable, or where negative pressure is desirable. In particular, these apparatuses and methods of using them may be useful for contracting a uterus to reduce hemorrhaging following childbirth.

Described herein are surgical drain apparatuses (e.g., systems, devices, etc.). For example, described herein are systems comprising: a first elongate member (also referred to herein an outer elongate member) having a first lumen; a second elongate member (also referred to herein as an inner elongate member) that is slidably disposed in the first lumen; an invertible porous mesh coupled at a first end to a distal end region of the first elongate member and at a second end to a distal end region of the second elongate member, wherein the invertible porous mesh has an expanded configuration, in which the invertible porous mesh is expanded to form a gap at least partially around the second elongate member; and retracted configuration in which the invertible porous mesh is inverted and withdrawn into the first lumen; and a vacuum channel extending from a proximal vacuum port to one or more distal vacuum openings positioned within the gap when the invertible porous mesh is in the expanded configuration.

Any of these apparatuses may include an expandable/contractible occluder that is either integrated with the other portions of the apparatus (e.g., the first elongate member) or separate from the other portions and configured to engage with the other portions. The occluder typically forms a seal around the apparatus so that the distal end (including the invertible porous mesh) may be sealed within the body region being treated so that negative pressure may be applied to the body region to drain the body region and/or to collapse the body region. Thus, the occluder may include a radially expandable and collapsible sealing region that may occlude and seal off the access, including anatomical access, into the body region (e.g., a canal, channel, incision, etc.). The occluder may have a channel or lumen that permits operation of the other components of the apparatus through the occluder, without disrupting the seal. For example, any of these apparatuses may include an occluder having an occluder lumen passing therethrough, wherein the occluder is configured to expand radially outward to seal a channel, further wherein the second elongate member is slidably disposed relative to the second lumen.

In some examples, the apparatus (e.g., system) may be configured as a surgical drain system comprising: a first elongate member having a first lumen, wherein the first elongate member is flexible and/or curved; a second elongate member that is slidably disposed in the first lumen; an invertible porous mesh coupled at a first end to a distal end region of the first elongate member and at a second end to a distal end region of the second elongate member, wherein the invertible porous mesh has an expanded configuration, in which the invertible porous mesh is expanded to form a gap at least partially around the second elongate member; and retracted configuration in which the invertible porous mesh is inverted and withdrawn into the first lumen; a vacuum channel extending from a proximal vacuum port to one or more distal vacuum openings positioned within the gap when the invertible porous mesh is in the expanded configuration; and an occluder having an occluder lumen passing therethrough, wherein the occluder is configured to expand radially outward to form a seal against a channel, further wherein the second elongate member is slidably disposed relative to the second lumen.

As mentioned, in some examples the occluder may be integrally formed as part of (or coupled to) the apparatus, such as to the first elongate member. For example, the occluder may be coupled to an outer surface of the first elongate member. The occluder may be configured as an expandable mesh to which a sealing membrane has been coupled; alternatively or additionally, the occluder may include a balloon. For example, an expandable mesh occluder may be configured so that the occluder includes a slidable proximal end configured to expand the occluder when driven distally, and to collapse the occluder when driven proximally. The distal end of the expandable mesh may be coupled to the outer surface of the first elongate member. Any of these apparatuses may include an actuator configured to expand and contract the occluder. The actuator may be a handle that can be slid proximally and withdrawn proximally. The actuator may be incrementally adjustable to hold the occluder open (or closed) to a selected amount.

In some examples the first elongate member comprises a flexible and/or curved tube. For example, the first elongate member may have a polymeric shaft that can be bent or curved to allow it to navigate bends within the anatomy. In some examples the first elongate member is pre-curved or pre-bent at one or more regions along its length. In some examples, the first elongate member is steerable over all or a portion of its length. For example the first elongate member may include one or more tendons to allow steering. The first elongate member may be any appropriate length. For example, the first elongate member may be between about 10 and 100 cm (e.g., between about 15 and 80 cm, between about 20 and about 50 cm, etc.). The first elongate member may be formed of a polymeric material and/or a metallic material.

The second elongate member may be flexible and/or bent (e.g. pre-bent or pre-curved) along all or a portion of its length. The second elongate member typically has a smaller outer diameter (OD) than the inner diameter (ID) of the first elongate member, as the second elongate member is slidably disposed within the first elongate member. The movement of the second elongate member within the first elongate member may be limited, and/or may include one or more (e.g. a plurality) of "stop" positions that may releasably hold the relative position of the second elongate member and the first elongate member.

The second elongate member may be formed as a solid member (e.g., a bar, rod, wire, etc.) or it may be hollow (e.g., a catheter, tube, etc.). The second elongate member may be a polymeric material and/or a metallic material, such as stainless steel, nitinol, etc.

Any of the invertible porous meshes described herein may be a knitted, woven, or braided material. In some examples, the invertible porous mesh is a non-woven material (e.g., such as a sheet or layer of polymeric material through which pores of sufficient size to allow passage of fluids and biological debris (e.g., pus, coagulate, etc.) to pass without significant resistance. In some examples the invertible porous mesh is a fabric. The invertible porous mesh may be formed of a plurality of filaments (e.g., strands) of material, such as monofilaments or multiple filaments. For example, the invertible porous mesh may comprise a braided polymeric monofilament having 24 or more strands (e.g., 30 or more strands, 34 or more strands, 36 or more strands, 38 or more strands, 40 or more strands, 42 or more strands, etc.).

The invertible porous mesh typically has a plurality of openings or pores that pores may be sufficiently large to allow fluids and some solid biological debris (e.g., clots, pus, coagulate) to pass easily. For example, the pore may have a pore diameter that is 0.1 mm or greater (0.2 mm or greater, 0.3 mm or greater, 0.4 mm or greater, 0.5 mm or greater, 0.6 mm or greater, 0.7 mm or greater, 0.8 mm or greater, 0.9 mm or greater 1 mm or greater, 1.1 mm or greater, 1.2 mm or greater, 1.3 mm or greater, 1.4 m or greater, etc.). The pores may be formed by the spaces between the strands, e.g., in woven, braided and/or knitted invertible porous meshes.

The invertible porous mesh may be expanded into a expanded configuration, as mentioned. In some examples the invertible porous mesh is biased to expand into the expanded configuration. For example, the invertible porous mesh may be formed of a shape memory material (e.g., nitinol, etc.) that can be shape set to an expanded configuration in which the invertible porous mesh is expanded away from the second elongate member, which is typically (unless it is inverted) extending within the chamber or pocket formed by the invertible porous mesh.

The invertible porous mesh may have a delivery configuration in which the invertible porous mesh is pulled taught against the second elongate member, e.g., by increasing the distance between the distal end regions of the first elongate member and the second elongate member. Since the ends of the invertible porous mesh are attached to these distal end regions, this will effectively pull the invertible porous mesh, allowing it to collapse down against the second elongate member, having a narrower profile, which may be desirable when positioning it. The invertible porous mesh may then be converted into the expanded configuration by reducing the spacing between the distal end of the first elongate member and the distal end of the second elongate member to set "expansion" position in which the invertible porous mesh is expanded radially outward, without inverting. For example, the distal end region of the second elongate member may be pulled slightly proximally. This may cause the invertible porous mesh to expand; in some cases it may allow the invertible porous mesh to expand outwards. In other examples it may allow the invertible porous mesh to stack up on itself. The expanded invertible porous mesh configuration may then be transitions into a retracted configuration in which the second of the invertible porous mesh is pulled into the channel or pocket formed by the invertible porous mesh (e.g., by pulling the second elongate member proximally). In some examples the invertible porous mesh may be completely inverted and pulled into the lumen of the first elongate member (while the first end of the invertible porous mesh remains attached distally to the distal end of the first elongate member).

Any of these apparatuses may be coated with one or more materials to enhance their biological efficacy. For example, these apparatuses may be coated with a clot-promoting material, such as aprotinin, tranexamic acid (TXA), epsilon-aminocaproic acid and aminomethylbenzoic acid. Thus, any of the invertible porous meshes described herein may include a clot-promoting material.

The vacuum ports may open out of the distal end of the first elongate member and/or out of one or more vacuum port openings through the distal end region of the second elongate member. In general, the vacuum port opens into the gap (e.g., the chamber or pocket) formed within the invertible porous mesh when it is in the expanded configuration. Because the invertible porous mesh include the pores configured to allow liquid and material to easily pass through, the invertible porous mesh may help distribute the force of the negative pressure within the body region (e.g., body cavity, such as a uterus, etc.). The invertible porous mesh in the expanded configuration may prevent local region of higher negative pressure that may otherwise seal up just portions of the body region preventing uniform draining.

For example, the vacuum port may be on a proximal end region of the first elongate member, and the vacuum channel extends within the first lumen and out of a distal end of the first elongate member. In some examples the vacuum port is on a proximal end region of the second elongate member and the vacuum channel extends through a second lumen in the second elongate member to exit from one or more sidewall channels through a distal end region of the second elongate member.

In general, the apparatus (e.g., system, device, etc.) may include one or more seals between the first elongate member and the second elongate member. The seals may be configured (e.g., shaped, positioned, formed of an appropriate material, etc.) to allow the first elongate member to slide within the lumen of the second elongate member, without requiring much force to slide. For example, the seals may be O-rings (or multiple O-rings), which may be lubricated or unlubricated.

As mentioned, the apparatuses (e.g., systems) may be configured to hold the relative position of the first elongated member, and the second elongate member. This may be done by a locking mechanism, such as a lock configured to secure (e.g., removably secure) the relative position of the first elongate member and the second elongate member. The lock may allow the relative positions to be held until additional force is applied to overcome the holding force. For example, the lock may be a ratcheting element at the proximal end of the apparatus (e.g., on or part of a handle at the proximal end).

Also described herein are methods of removing material (e.g., fluid) from a body region and/or contracting a body region using any of the apparatuses described herein. These methods may be methods of draining the body region and/or contracting the body region. These methods may be method of reducing hemorrhaging. Any appropriate body region may be treated as described. For example, the body region may be a uterus, and the method may be a method of contracting a uterus to reduce hemorrhaging. The body region may be a wound, and the method may be a method of enhancing healing by draining the wound and/or reducing hemorrhaging and/or enhancing healing. For example, these methods and apparatuses may be used following a breast surgery, treating (e.g., draining) a chest wound, a hernia, etc.

For example, described herein are methods of draining a body region, the method comprising: positioning a distal end of an invertible porous mesh into the body region, wherein the invertible porous mesh is coupled at a first end to a distal end region of a first elongate member and at a second end to a distal end region of a second elongate member that is slidable disposed within a lumen of the first elongate member; expanding the invertible porous mesh within the body region to form a gap at least partially around the second elongate member creating a seal to maintain a vacuum within the body region; applying negative pressure from one or more vacuum ports opening into the gap of the expanded invertible porous mesh; withdrawing the second elongate member proximally to invert the invertible porous mesh as the invertible porous mesh is pulled into the lumen of the first elongate member; and maintaining the negative pressure within the body region to mitigate hemorrhaging.

As mentioned, in some examples the method is a method of contracting a uterus to reduce hemorrhaging, the method comprising: positioning a distal end of an invertible porous mesh into the uterus, wherein the invertible porous mesh is coupled at a first end to a distal end region of a first elongate member and at a second end to a distal end region of a second elongate member that is slidable disposed within a lumen of the first elongate member; expanding the invertible porous mesh within the uterus to form a gap at least partially around the second elongate member; creating a seal to maintain a vacuum within the uterus; applying negative pressure from one or more vacuum ports opening into the gap of the expanded invertible porous mesh; withdrawing the second elongate member proximally to invert the invertible porous mesh as the invertible porous mesh is pulled into the lumen of the first elongate member; and maintaining the negative pressure within the uterus to mitigate uterine hemorrhaging.

In any of these methods, expanding the invertible porous mesh may include reducing the distance between the distal end region of the first elongate member and the distal end region of the second elongate member. Reducing the distance between the distal end region of the first and second elongate members may include one or both of moving the first elongate member distally over the second elongate member and moving the second elongate member proximally within the first elongate member.

Expanding the invertible porous mesh may include expanding the invertible porous mesh more in one direction than another. In any of the devices described herein, the porous mesh may be soft compliant, particularly when expanded. Thus, any of these methods may include conforming the porous mesh within the body region being treated; this may include flattening the porous mesh.

In any of the methods described herein, creating the seal may comprise expanding an occluder that is positioned on a proximal region of the first elongate member. Expanding the occluder may comprise inflating the occluder with saline and/or expanding a mesh to which a sealing member is coupled.

Applying negative pressure may comprise applying suction from a distal end of the first elongate member. In some examples applying negative pressure comprises applying suction from one or more openings through a sidewall of the distal end region of the second elongate member.

In general, these methods may include distributing a force of the vacuum to compress the body region by applying negative pressure from out of the invertible porous mesh when applying negative pressure from one or more vacuum ports opening into the gap of the expanded invertible porous mesh.

The negative pressure within the body region may be maintained for any appropriate length of time. For example, the negative pressure may be maintained for 1 minute or longer (e.g., 2 minutes or longer, 5 minutes or longer, 10 minutes or longer, 15 minutes or longer, 20 minutes or longer, 25 minutes or longer, 30 minutes or longer, 45 minutes or longer, 1 hour or longer 1.5 hours or longer, 2 hours or longer, 3 hours or longer, 4 hours or longer, 5 hours or longer, 6 hours or longer, 7 hours or longer, 8 hours or longer, etc.) after the invertible porous mesh is pulled into the lumen of the first elongate member.

In any of these methods, the distal end of the invertible porous mesh may be positioned within the tissue to be treated, such as, e.g., within the uterus.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 6A-6D show another example of an apparatus configured as a rolling drain.

FIGS. 12A-12C illustrate operation of another example of a rolling drain apparatus.

FIGS. 15A, 15C, and 15E show side views and FIGS. 15B, 15D and 15F show end views.

FIG. 16A-16B show an example of a distal end of a rolling drain as described herein, including a soft obturator portion.

FIG. 17 shows an example of an apparatus as described herein including a trocar at the distal end.

FIG. 18A schematically illustrates one example of a method of draining fluid from a body region as described in greater detail here.

DETAILED DESCRIPTION

Figure 1A:
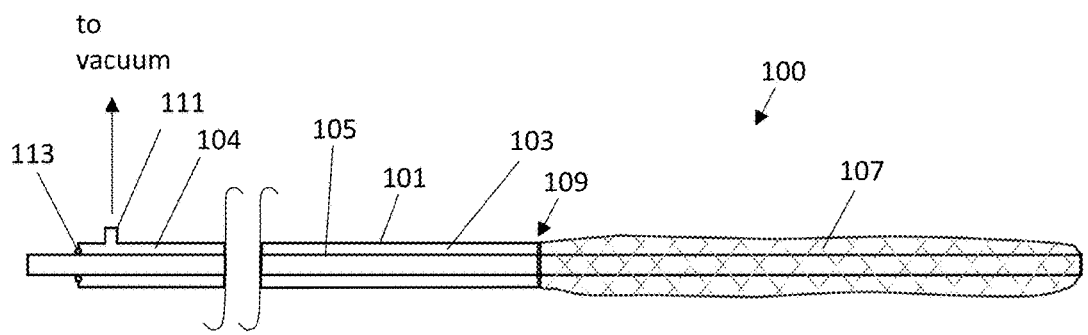
FIGS. 1A-1E illustrate one example of an apparatus configured as a rolling drain as described herein.

Described herein are methods and apparatuses for draining a region of a body, in order to remove fluid or material from the region and/or contracting the region. This treatment may prevent or reduce bleeding and/or may otherwise enhance healing. These apparatuses and methods, including methods of using them may, may be particularly useful for forming regions of uniform negative pressure within soft tissue, and sustaining the negative pressure while atraumatically removing a portion of the apparatus (e.g., the invertible porous mesh) from between the soft tissue.

For example, described herein are apparatuses, including surgical drain systems, that include as part of the drain an invertible porous mesh that may be expanded within the body region being treated, and may be used to distribute the negative pressure (e.g., suction) applied by the apparatus within the region being treated. For example, the negative pressure may be applied out of the region (e.g., chamber, pocket, etc.) formed by the invertible porous mesh, through the pores of the mesh. These apparatuses may also include a seal or closure that may allow the treated region to retain the negative pressure within the body region. Finally these apparatuses are configured so that once the negative pressure is applied (and maintained) the invertible porous mesh may be gently removed by inverting over itself and drawing into the device.

These apparatuses (systems and devices) may generally include a delivery configuration having a relatively small OD that prevents or reduces trauma when the apparatus is inserted into the tissue. Similarly, the apparatus, and particularly the negative-pressure distributing invertible porous mesh may be withdrawn by rolling back into itself and into an elongate member of the apparatus to remove it from within the body region, even while applying negative pressure or while maintaining the negative pressure. The invertible porous mesh may be inverted gently, resulting in very low force as compared to pulling or dragging such as structure out of the tissue region, such as a pocket of tissue, resulting in less pain and/or trauma to the tissue.

As mentioned, these apparatuses may generally include an invertible porous mesh that distributes the negative pressure more effectively than existing surgical drains, and in particular active drains that apply negative pressure. The invertible porous mesh is typically and compliant and may conform to the region of the tissue into which it is positioned. As will be described in more detail herein, the apparatus, including an invertible porous mesh may be placed during surgery before surgical site closure.

For example, the invertible porous mesh may be pushed, or otherwise advanced and/or positioned, to remove fluid from a body region. Any tissue of the body may be treated with the rolling drains described herein. In particular, soft tissue regions, such as a pocket, chamber, opening, etc. formed or naturally present in tissue. The soft tissue to be treated may be a surgically-formed or traumatically formed region of the body, such as a tunneling wound, dead space, seroma forming pocket (surgical wound), etc. For example, the soft tissue to be treated may be a cavity formed by removal of a tumor or other tissue. In some examples, the soft tissue to be treated may be a natural orifice space (bladder, intestine, stomach, uterus, chest cavity, lungs, blood vessel, etc.) or the like. For example, the soft tissue to be treated may be a uterus.

The invertible porous mesh may be removed by first inverting it and drawing it back into the apparatus. The peeling removal force will generally be lower (by one or more orders of magnitude) than drag force needed for current drains. Further, the apparatuses described herein may include invertible porous mesh formed of inverting textile/fabric/sheath. The invertible porous mesh (e.g., fabric/sheath) typically communicates with the inner drain (e.g., the vacuum port coupled to the vacuum channel, so that the negative pressure is applied out of the invertible porous mesh. This will allow the invertible porous mesh (e.g., fabric/sheath) to distribute negative pressure to a greater area and/or to create a larger surface area for fluid control. Any of these invertible porous meshes may be porous. The porosity (e.g., the space between filaments in variations in which the invertible porous mesh if formed of knitted, woven or braided fibers) may be controllable. Any of these invertible porous meshes may be self-expanding (e.g., formed of a material such as Nitinol, nitinol mixed with polymers, etc.).

Any of the apparatuses described herein may have axial flexibility, so that they can be bent around structures or non-uniform volumes. In variations in which the apparatus may be introduced into a body orifice through a native or natural channel, such as for treating a uterus by passing through the vaginal canal.

The invertible porous mesh may be round/cylindrical, flat, oval cylinder. As mentioned, any of these apparatuses may be compliant. For example, an invertible porous mesh may be formed of "fabric" that is a knit, a weave, a braid, a non-woven sheet (e.g., polymer or metallic or mixes) material having pores formed through the sheet, etc. For example, in variations in which the invertible porous mesh is formed of a braided material, the brain may include any number of filaments, e.g., between 24-144 ends/filaments (e.g., between about 24-128 filaments, between about 32-98 filaments, etc.). In some examples, the filaments are formed of a material such as PET, Nylon, PP, Nitinol, Steel, Elgiloy, or some combination of these. The filament may be any appropriate diameters, such as between 0.003" to 0.025" diameter filaments (e.g., monofilaments or compound filaments). In some examples the invertible porous mesh if formed of filaments (knit, woven, braided, etc.) of between 100-2000 denier (e.g. multifilament or monofilament).

The rolling drain apparatuses described herein may be scaled to a variety of appropriate sizes in order to treat soft tissue regions of different sizes and shapes. For example, in some variations the invertible porous mesh portion may be between 10 cm and 100 cm long in the delivery configuration (e.g., proximal to distal length). In examples in which the rolling drain is formed of a sheet of material having pores formed through it, the sheet may be a film with slits, holes, slots, shaped holes, etc. formed through the sheet in a pattern. The pattern pores in the invertible porous mesh may be uniform or non-uniform, and may have an average pore density (porosity) as a percentage of 50% or greater (e.g., 60% or greater, 65% or greater, 70% or greater, 75% or greater, 80% or greater, 85% or greater, 90% or greater, 95% or greater, etc.).

Thus, as used herein the term "mesh" is not limited to structures formed by one or more strands, but may be formed of a non-woven material. The material forming the invertible porous mesh may be a porous filtering material such as Tyvek, filter paper, etc. or it may be (initially) non-porous and pores may be formed therein. The term "mesh" may refer to a material having an average porosity of greater than 50% that may be formed into an inverting structure that is sufficiently compliant so that it may invert back over itself. The invertible porous mesh may be formed as a tubular or basket shape (e.g., open at both ends or closed at one end (e.g., the distal end). The invertible porous mesh may be shaped into a generally tubular shape (open at one or both ends) that has an inner diameter that is larger than the outer diameter of the second, inner, elongate member to which the distal end of the invertible porous mesh is attached, and the second, inner, elongate member may be positioned within the inner region formed by the invertible porous mesh.

The space in the inner region of the invertible porous mesh between the inner, elongate member and the internal sides of the invertible porous mesh may be referred to as a "gap". For example, the invertible porous mesh may define an internal space within which the negative pressure (suction or vacuum) may be applied. As described in greater detail here, the negative pressure may be applied from one or more vacuum port (also referred to as suction ports) along a portion of the length of the second, inner, elongate member and/or out of the distal end opening of the first, outer, elongate member. Alternatively or additionally a separate vacuum line (e.g., suction line, such as tubing) may be inserted into the internal space of the invertible porous mesh.

The surgical drain systems may be configured so that the suction (negative pressure or vacuum) is applied through the invertible porous mesh from a distal end opening of the first (e.g., outer) elongate member, as shown in FIGS. 1A-1E. In FIGS. 1A-1E, the surgical drain system 100 includes a first elongate member 101 (shown as an outer elongate member) having a lumen 103 extending in a proximal to distal direction. The elongate member may be a catheter. In general, this elongate member may be any appropriate length so that it may be manipulated and positioned within the body region being treated. For example, the elongate member may be between 5 cm and 100 cm long (e.g., between 10 cm and 50 cm, between 10 cm and 35 cm, etc.). The elongate member may be a tube, such as a polymeric tube. The elongate member may be straight (as shown) or curved, including curved with a fixed curve (e.g., between 10-80 degrees). In general, the elongate member may be flexible.

The surgical drain system in this example also includes a second elongate member (e.g., an inner elongate member) 105 that is slidably disposed, e.g., can be slid distally and proximally) within the lumen of the first, outer, elongate member. The second elongate member may be solid or hollow, and may be as flexible or more flexible than the first elongate member. The second elongate member in FIGS. 1A-1E is shown as a rod, but may be a wire, microcatheter, etc. Either the first and/or the second elongate member may be configured to preferentially bend in one direction more than another, e.g., by including cuts or hinge regions.

In any of these examples the proximal direction may be the direction towards the hand of the user (e.g., physician, surgeon, medical technician, nurse, etc.) operating the device, and distal may be the direction away from the hand of the user.

The apparatus shown in FIGS. 1A-1E also includes an invertible porous mesh 107 that is coupled at a first (e.g., proximal in FIG. 1A) end to a distal end region 109 of the first elongate member. The invertible porous mesh is also attached and at a second (distal in FIG. 1A) end to a distal end region of the second elongate member. The invertible porous mesh shown in FIG. 1 is schematically illustrated as braided or woven mesh that includes a pattern of strands or fibers that are arranged with open pores. In general, the invertible porous mesh may be any of the invertible porous meshes described herein, including knit, woven, etc. or a sheet of nonwoven material into which pores have been formed. In FIG. 1A, the invertible porous mesh has a porosity of greater than 50% (e.g., in the schematic shown, the porosity is greater than 95%), and the pores are distributed across the entire invertible porous mesh. The invertible porous mesh is flexible.

The apparatus shown in FIGS. 1A-1E also includes a proximal region including a proximal vacuum port 111 that is configured as a connection to a source of negative pressure (e.g., vacuum). In some examples the vacuum port may be a mating connection (a sealing mating connection) to couple to tubing or the like for connecting to the source of negative pressure. In some cases the vacuum port, which may also be referred to as a suction port, may include a lock (e.g., leur-type lock) for opening/closing (to allow on/off of the negative pressure, and/or to maintain or hold the pressure already applied). In FIGS. 1A-1E the vacuum port formed on the outer surface of the first (e.g., outer) elongate member at the proximal end region. Alternatively the vacuum port may extend from the elongate member, via a tube or channel (not shown). As described for FIGS. 2A-2C, below, in some examples the proximal vacuum port may be coupled or connected to a second (inner) elongate member. In some examples, both the inner lumen of the first elongate member and the second elongate member may be used as a vacuum channel. In FIGS. 1A-1E, the inner lumen of the first (outer) elongate member is configured as the vacuum channel.

In general, the lumen 103 of the first elongate member may be the vacuum channel or a dedicate vacuum channel (not shown) may run through the lumen of the first elongate member. For example, a tube (not shown) connected to the vacuum port 111 may be configured as the vacuum channel and may extend the length of the lumen of the first elongate member so that the opening of the vacuum channel may open into the space formed within the invertible porous mesh. Alternatively, as shown in FIG. 1A, the lumen of the first elongate member forms the vacuum channel 104 (e.g., is continuous with the vacuum channel) extending from the proximal vacuum port 111 to one or more distal vacuum openings at the distal end of the first elongate member 109. In this example, the lumen is sealed at the proximal end by one (or in some cases, more than one) seal 113. In FIG. 1A, the seal is shown (by section) schematically as an O-ring that allows the second elongate member 105 to slide distally and proximally relative to the outer elongate member while maintaining the seal and the vacuum within the vacuum channel (in this example, within the lumen of the first elongate member).

Since the invertible porous mesh 107 is attached to the distal end region of the first elongate member 101, the distal vacuum opening (suction inlet) is positioned within the gap of the invertible porous mesh. The gap is the region within the invertible porous mesh formed when the invertible porous mesh is in the expanded configuration, as shown in FIGS. 1B-1C.

FIG. 1A shows the apparatus in a delivery configuration, in which the invertible porous mesh extended distally, and the second elongate member 105 extended distally relative to the first elongate member 101. In this configuration the invertible porous mesh may be held against (or near) the outer diameter of the second elongate member, as shown. In some examples the apparatus may include a lock or latch mechanism to hold the relative positions of the first and second elongate member (and thus the configuration of the invertible porous mesh) of these configurations (e.g., delivery configuration, deployed configuration, retracted configuration, or intermediate positions of any of these). For example the proximal end of the device may include a handle (not shown) with a control, such as a slider, wheel, dial, etc.) that may be configured to move the first elongate member relative to the second elongate member. The handle may include a lock or latch to releasably hold the relatively positions of the first and second elongate members until they are actively moved by the user.

Figure 1B:
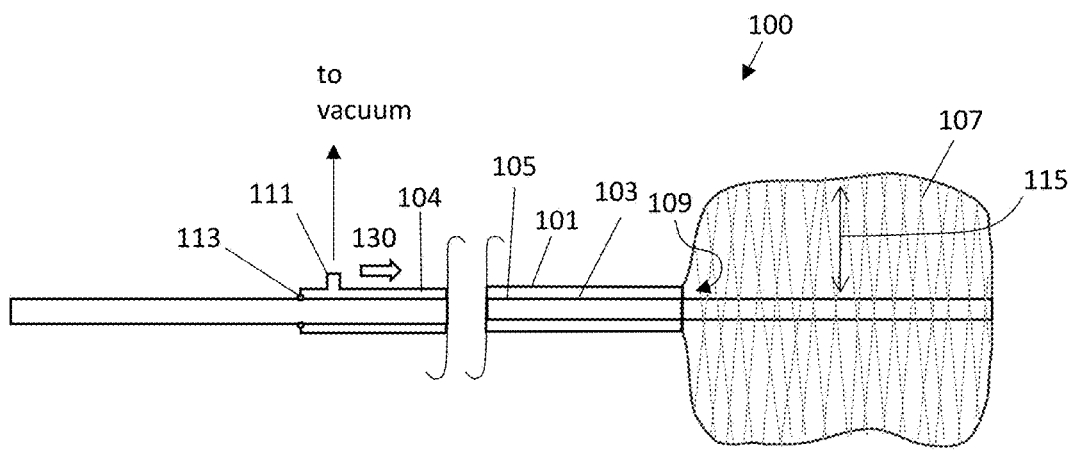
Figure 1C:
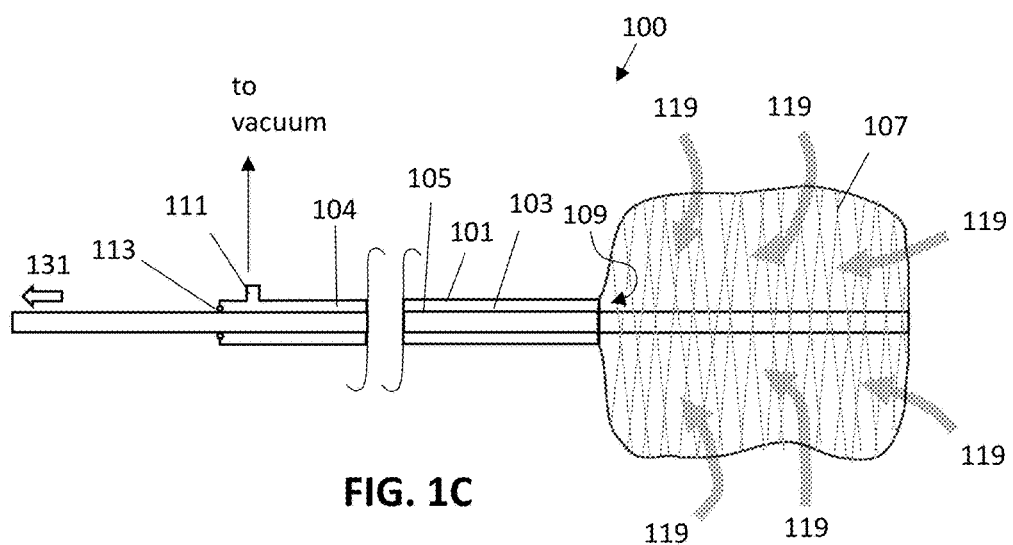

In general, the apparatus shown in FIG. 1A may be converted to a deployed configuration, in which the invertible porous mesh is expanded outward from the second member, as shown in FIGS. 1B and 1C. This may be accomplished by moving the first, outer, elongate member distally, as shown by the arrow 130 in FIG. 1B, or by moving the second, inner, elongate member proximally, as shown by the arrow 131 in FIG. 1C, or both. In the expanded configuration, the invertible porous mesh is radially expanded outward from the second elongate member but not inverted. In both FIGS. 1B and 1C the invertible porous mesh may be expanded in part by allowing the invertible porous mesh to return to a shape set (expanded) configuration and/or by moving the first elongate member and/or the second elongate member to reduce the distance between the first and second ends of the invertible porous mesh. In some examples, the invertible porous mesh may expand outward as it stacks up on itself; at some point, (as described in reference to FIGS. 1D and 1E) the invertible porous mesh may invert into itself, however for deployment (e.g., expansion) the relative motion of the first and second elongate members may be limited so that the invertible porous mesh expands, but stops before it inverts. The invertible porous mesh is expanded outward and forms a gap 115 at least partially around the second elongate member. The gap may be non-uniform. Since the invertible porous mesh is expanded out into the tissue region, it may conform somewhat as it expands, to fit the opening; the invertible porous mesh may be biased (e.g., may be shape-set) to the expanded configuration in a uniform or non-uniform expansion around the second elongate member. However, even when shape set may still be compliant enough to compress (as shown and described in FIG. 2C, below) or otherwise confirm to the general shape of the opening in the body region being treated. Fluid and material within this tissue region may pass through the pores into the space formed by the expanding invertible porous mesh, even without applying negative pressure yet; once negative pressure is applied, fluid and material (particles, mucus, clot, pus, etc.) within the space may be drawn into the gap and into the suction port(s). This is schematically illustrated in FIG. 1C, showing the negative pressure (119, shaded arrows) pulling fluid and material within the cavity into the vacuum port, through the invertible porous mesh 107. In practice, the negative pressure may cause the soft tissue to compress around the invertible porous mesh; the invertible porous mesh may the tissue from collapsing just around the one or more vacuum ports and may allow a more uniform compression of the tissue.

Figure 1D:
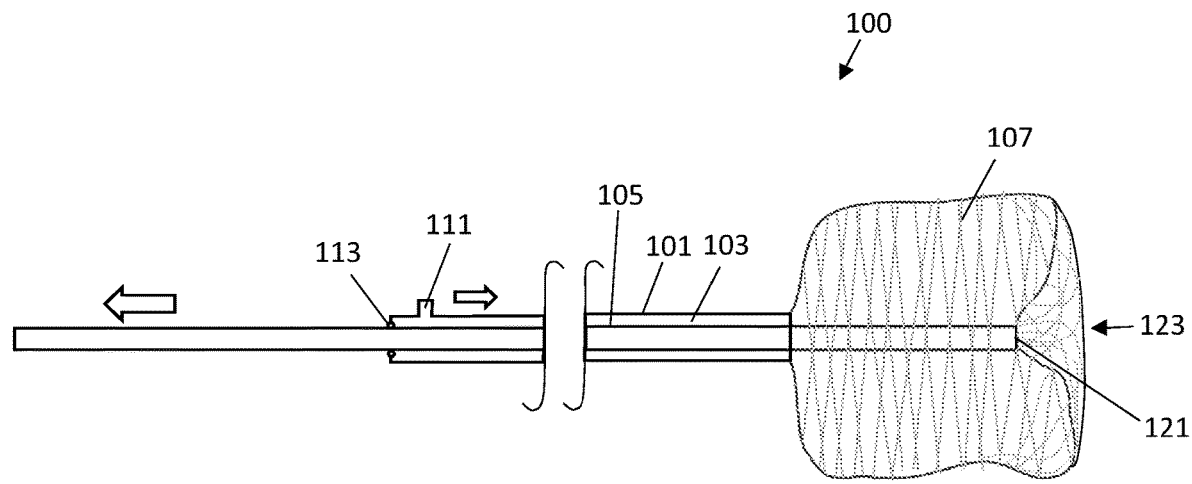

In general, the invertible porous mesh may be deployed in the tissue region and negative pressure applied. In any of the methods of use described herein the tissue region may be blocked or sealed off (as will be described in greater detail below) to allow the negative pressure to be maintained within the soft tissue. As mentioned, the invertible porous mesh may help distribute the force of the negative pressure. During the application of negative pressure (or in some cases, after a desired amount of negative pressure has been applied), the invertible porous mesh may be withdrawn, while leaving the apparatus, including (in some examples) the seal or occluder maintaining the negative pressure in place. FIG. 1D illustrates the retraction of the invertible porous mesh by inverting the invertible porous mesh into itself as it is withdrawn from the distal end into the first (outer) elongate member 101 by pulling on the second (inner) elongate member 105 so that it is withdrawn into the lumen 103 of the first elongate member. As shown the distal end region 121 of the invertible porous mesh is attached to the distal end region of the second (inner) elongate member causing the invertible porous mesh to invert into itself 123 as shown.

Figure 1E:
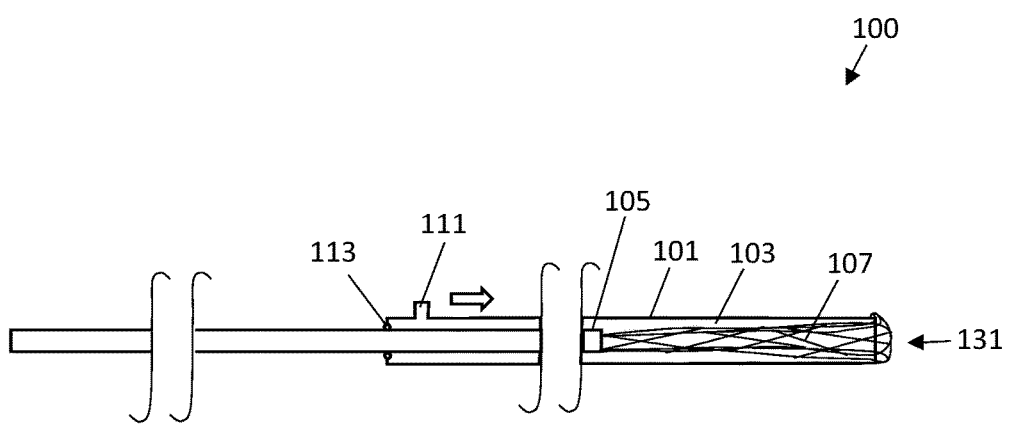

In FIG. 1E the invertible porous mesh 107 is shown fully inverted 131 and held within the lumen of the first elongate member 101. FIG. 1E shows the invertible porous mesh in a retracted configuration in which the invertible porous mesh is inverted and withdrawn into the first lumen.

FIGS. 2A-2D illustrate another example of an apparatus similar to that shown in FIGS. 1A-1E, but with a plurality of vacuum ports on the second (inner) elongate member, so that the lumen of the second elongate member acts as a vacuum channel. Alternatively a separate vacuum channel (e.g., flexible tube, not shown) may be present in the second elongate member.

Figure 2A:
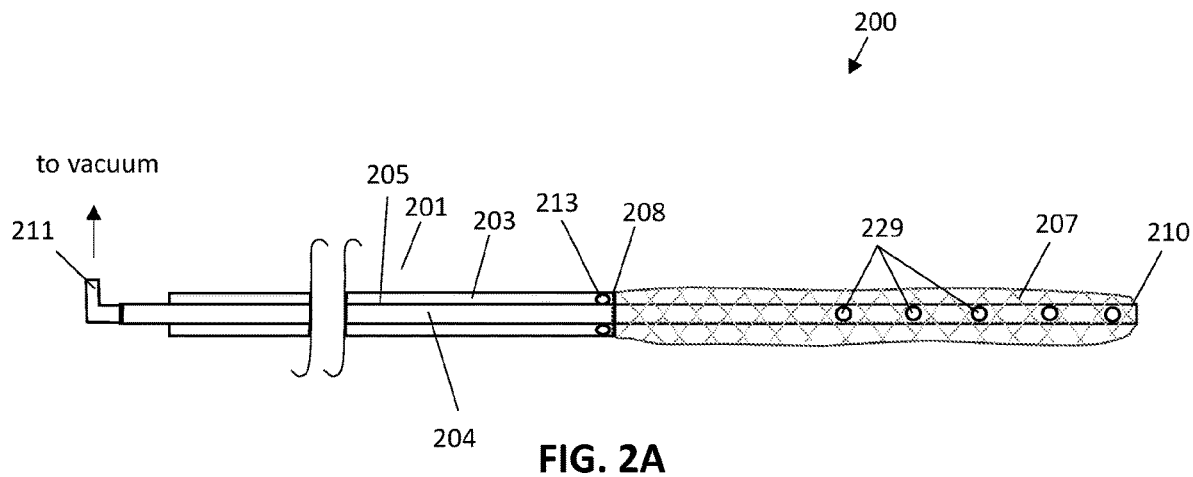
FIGS. 2A-2D illustrate an example of an apparatus configured as a rolling drain as described herein.
Figure 2B:
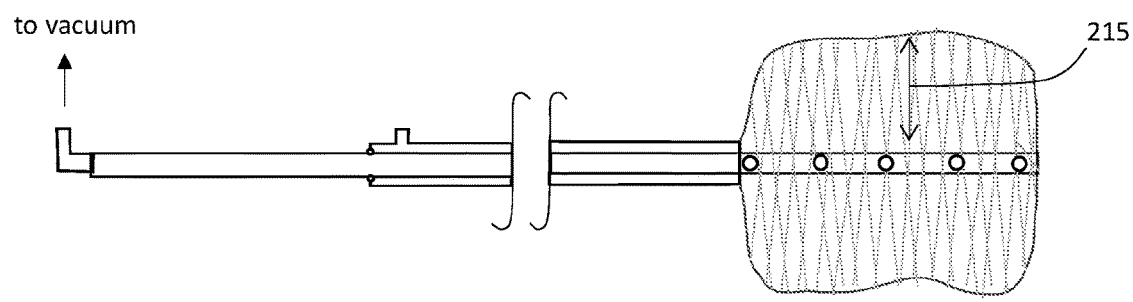

In FIG. 2A, the apparatus 200 includes a first (e.g., outer) elongate member 201 having a first lumen 203, wherein the first elongate member is flexible and/or curved; in FIG. 2A the first elongate member is flexible but is straight. The apparatus also includes a second (e.g., inner) elongate member 205 that is slidably disposed in the first lumen. The invertible porous mesh 207 is attached at a first end to a distal end region 208 of the first elongate member and at a second end 210 to a distal end region of the second elongate member. In FIG. 2A the invertible porous mesh is shown with the apparatus in a delivery configuration, with the first (proximal) end separated from the second (distal) end so that the invertible porous mesh is pulled close to the second (inner) elongate member. In FIG. 2B the invertible porous mesh is expanded with the apparatus in an expanded configuration, in which the invertible porous mesh is expanded radially out from the second elongate member 205 to form a gap 215 at least partially around the second elongate member. As in FIG. 1D, the invertible porous mesh may be fully inverted and retracted into the lumen of the first elongate member in a retracted configuration.

In FIGS. 2A-2B the apparatus shows the vacuum channel 204 extending from a proximal vacuum port 211 on the proximal end of the second (inner) elongate member 205 to a plurality of distal vacuum openings 229 on the distal end of the second elongate member. The vacuum openings are arranged along the length of the second elongate member in this example, and are positioned within the spaced formed by the invertible porous mesh, e.g., in the gap 215 formed when the invertible porous mesh is in the expanded configuration.

Figure 2C:
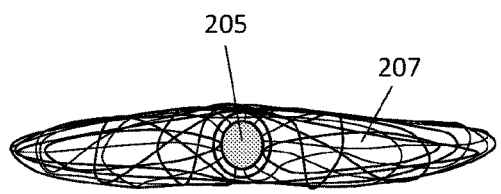
Figure 2D:
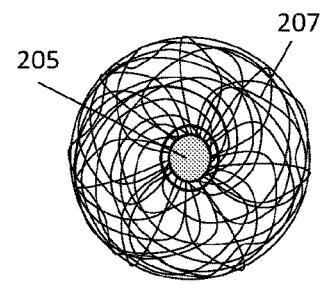

FIG. 2C is a distal end view of the apparatus of FIGS. 2A-2B (which is similar or identical to a same view of the apparatus of FIGS. 1A-1E), in which the expanded invertible porous mesh is compressed, a compared to FIG. 2D, showing the same viewpoint (distal end view) with the invertible porous mesh in a symmetrically fully expanded configuration (e.g., outside of the body). In FIG. 2C the invertible porous mesh 207 is coupled to the distal end region of the second elongate member 205.

Figure 3A:
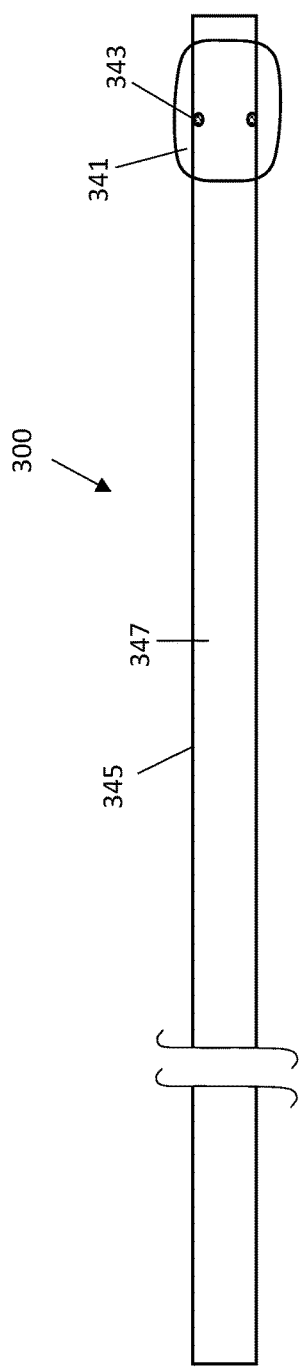
FIGS. 3A-3B illustrate an example of an occluder that may be use with (or integrated into) a rolling drain apparatus as described herein.
Figure 3B:
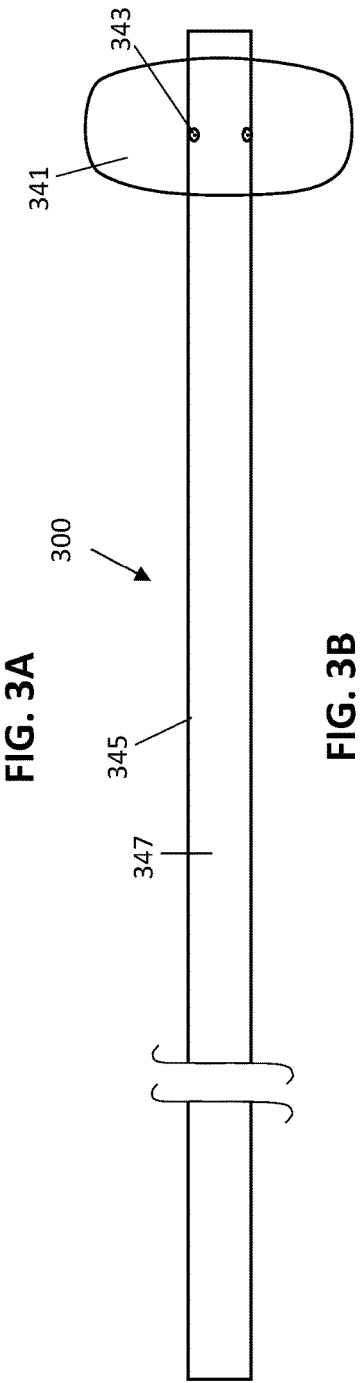
Figure 4A:
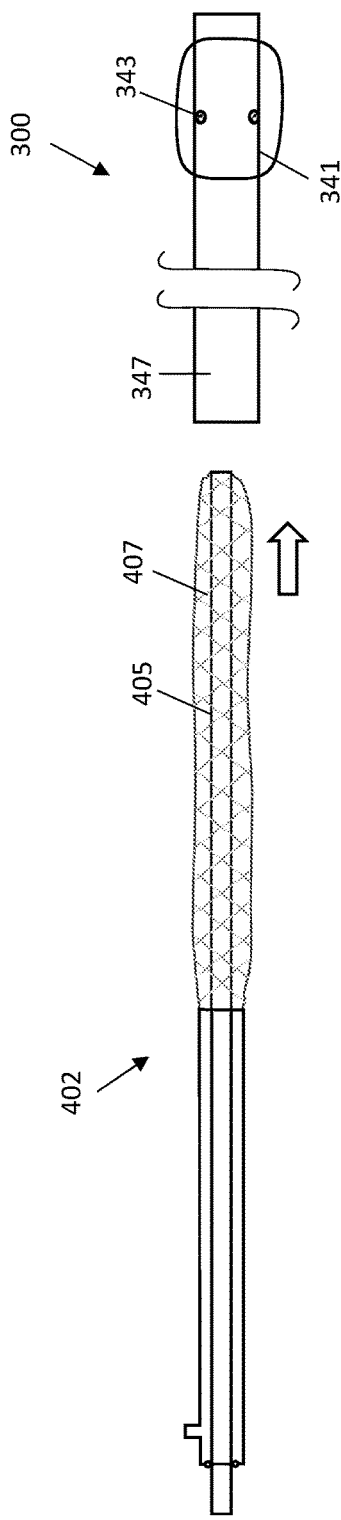
FIGS. 4A-4D illustrate the use of an occluder such as the one shown in FIGS. 3A-3B with a rolling drain to form a rolling drain system as described herein.

Any of these apparatuses may include an occluder. The occluder may seal off the body region so that the negative pressure delivered by the apparatus into the body region may be maintained. The occluder may be part of the same apparatus, including integrally attached, e.g., to the first elongate member or other region, or it may be a separate component that engages with the other portion(s) of the system, including a rolling surgical drain such as those shown in FIGS. 1A-1E and 2A-2D. FIGS. 3A-3B shows an example of an occluder 300 portion of an apparatus. In general, the occluder may include an elongate tubular body 345 (e.g., a catheter body) that may allow passage of the other components of the surgical drain. Any of the occluders described herein may include an expandable/collapsible occluding seal 341 region that can be activated to expand to seal off of the region of the body in which the apparatus is treating. In FIGS. 3A-3B the occluding seal 341 is shown as an expandable balloon that can be expanded from a collapsed configuration, shown in FIG. 3A, to an expanded configuration, shown in FIG. 3B. FIG. 4A shows the occluder 300 of FIGS. 3A-3B engaging a rolling surgical drain 402 similar to those shown in FIGS. 1A-1E and 2A-2D. In this example, the rolling surgical drain may be inserted into a lumen of the occluder with the invertible porous mesh 407 held against the second elongate member (the rolling surgical drain is in the delivery configuration); once inserted in to the occluder, one or more seals 343 (shown as an O-ring in FIGS. 3A-3B and 4A-4D). In general, the occluder includes an occluder lumen 347 passing therethrough, wherein the occluder is configured to expand radially outward to form a seal against a channel, further wherein the second elongate member is slidably disposed relative to the second lumen. Thus, the rolling surgical drain may be sealed within the body region when the occluder is sealing against the tissue. In some examples the expandable occluder may be a foam, sponge or other material that may expand to seal as described herein. The occluder may include a fluid-impermeable membrane over the expandable element (e.g., foam, frame, balloon, etc.).

Figure 4B:
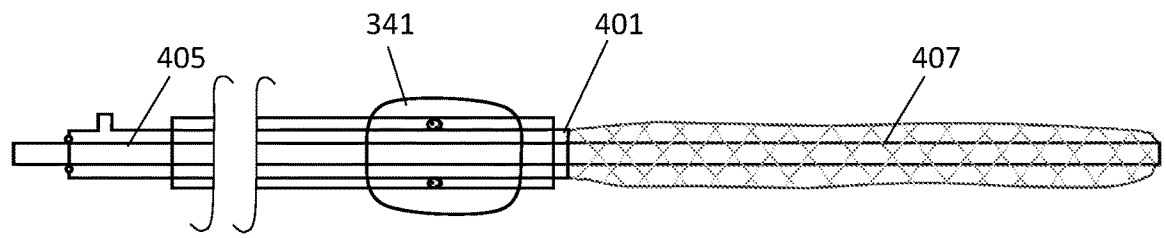
Figure 4C:
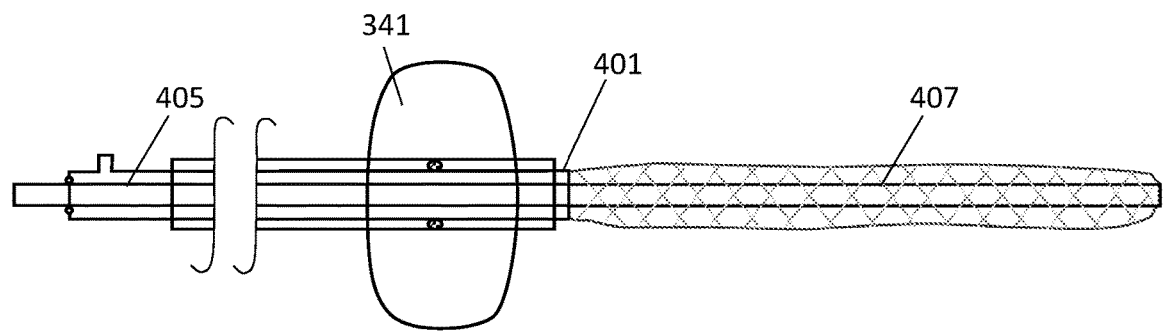
Figure 4D:
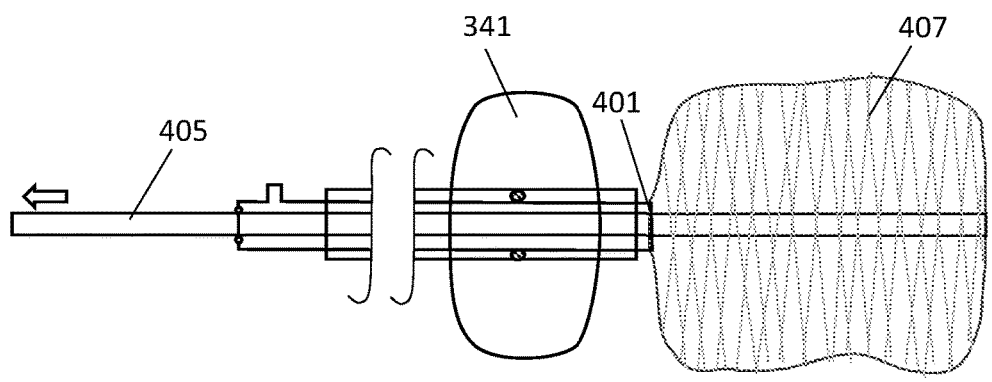

FIGS. 4B-4D illustrate operation of the apparatus including the occluder 300 and the rolling surgical drain 402 shown in FIG. 4A. In FIG. 4B the rolling surgical drain is extended distally out of the occluder, and the occluder and the drain may be inserted together into the body region to be treated. Alternatively in some examples the occluder may be inserted first and the rolling surgical drain may be inserted into the body. The occluder may therefore act as an introducer, and/or may be used with visualization.

In FIG. 4C the occluder occluding seal 341 of the occluder is expanded into a sealing configuration. The occluding seal may be expanded mechanically, e.g., by including an expandable frame or mesh, as will be illustrated in more detail below, and/or it may be expanded by filling with a fluid (gas, liquid, etc., such as saline). The diameter of the occluding seal is larger, allowing it to seal against the tissue through which the device was introduced. Once sealed and/or anchored in position, the rolling surgical drain may be actuated as described above. For example, in FIG. 4D the invertible porous mesh 407 is shown deployed out. In this example the distal end of the first elongate member 401 is extended slightly out of the occluder and the vacuum port may be at the distal end of the elongate member within the invertible porous mesh, as described above. Alternatively or additionally, one or more vacuum ports may be formed through the second (inner) elongate member 405, as shown in FIGS. 2A-2B.

Figure 5A:
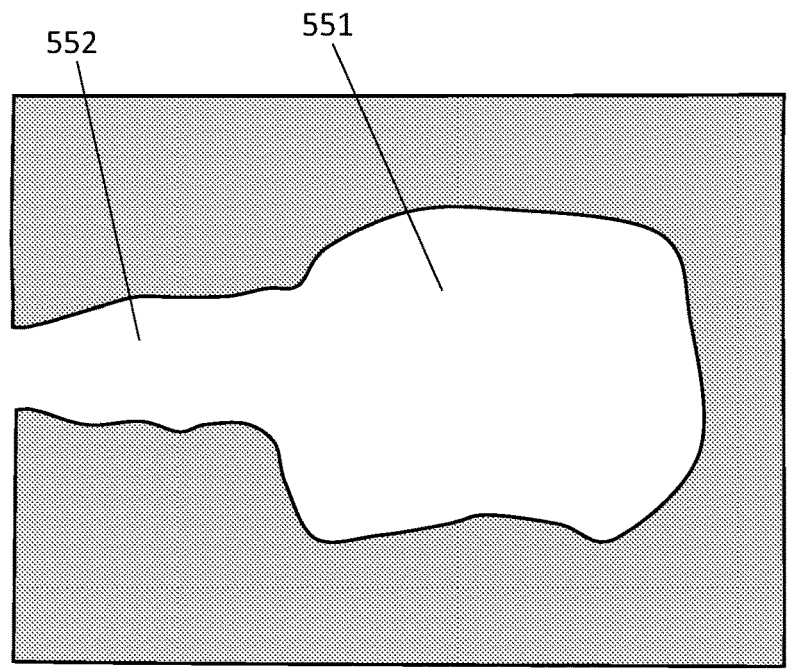
FIGS. 5A and 5B illustrate one example of a method of treating a tissue region as described herein.

For example, FIG. 5A shows an example of soft tissue region 551 within a body that may be treated as described herein. The soft tissue region may be a surgical site (e.g., the site of removal of a tumor, for example, or a body lumen, such as a postpartum uterus, including a portion of the vaginal canal.

Figure 5B:
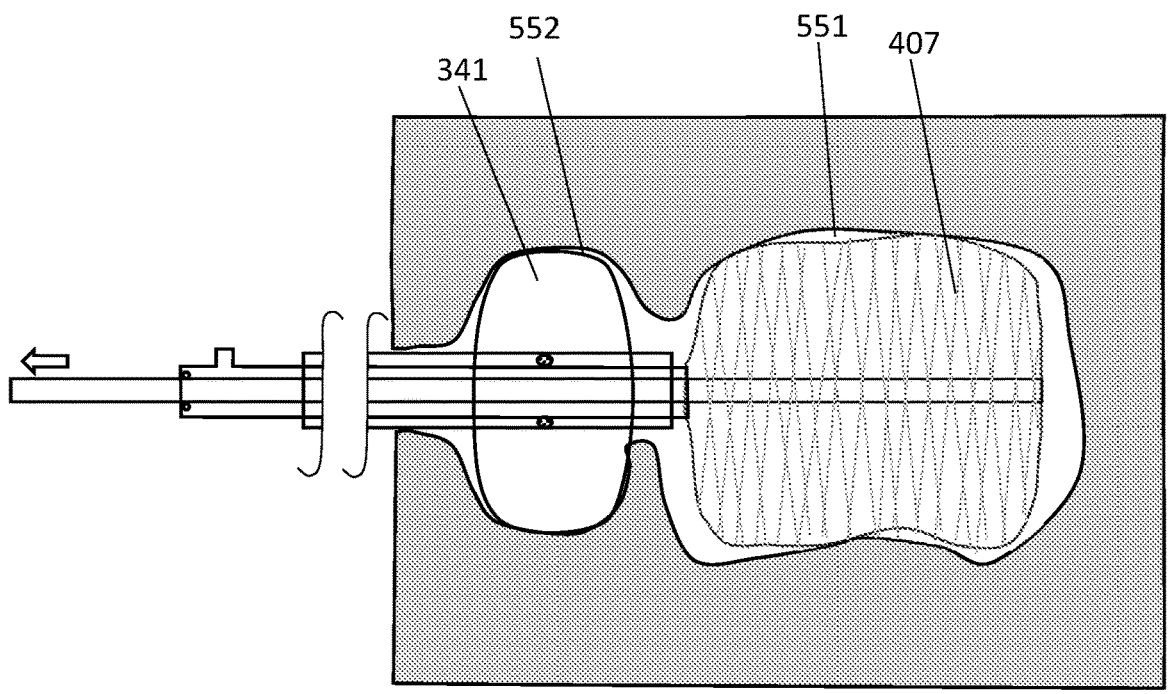

The apparatus may be inserted into the soft tissue region to be treated, e.g., by inserting the distal end of the apparatus through the channel or canal 552, and the apparatus deployed as described above. In FIG. 5B the apparatus is shown with the occluding seal 341 of the occluder expanded to seal the apparatus within the soft tissue, so that vacuum (negative pressure) may be applied by the apparatus and the soft tissue region 551 may be held under the negative pressure. Within the soft tissue region, the invertible porous mesh 407 may be expanded outwards so that the vacuum may be applied through the invertible porous mesh.

FIGS. 6A-6D illustrate another example of an apparatus as shown herein in which the rolling surgical drain includes an integral occluder (occluding seal portion) 641 coupled to the first elongate member 601. In this example the occluding seal portion 641 of the occluder is formed by a tubular sheet or mesh (e.g., woven, knit, braided, non-woven sheet, etc.) that is sealed. For example, the mesh may include a laminated polymeric sheet. The distal end 622 of the occluding seal portion is fixed to the surface of the first (e.g., outer) elongate member 601, and an occluder deployment member 661 that is slidably disposed over the first elongate member 601. As shown in FIG. 6B, the occluder may be deployed and expanded outward to form a seal by driving the occluder deployment member 661 distally (shown by arrow 681).

The apparatus shown in FIG. 6A also includes an invertible porous mesh 607. As mentioned above, the mesh may be formed of a knit, woven or braided material (or a porous sheet of non-woven material) having pores. In one example the invertible porous mesh is formed of a braided monofilament of polypropylene (e.g., 0.015-0.02") filament, using, e.g., 48 strand/ends. The invertible porous mesh may be actuated by pulling on second (e.g., inner) elongate member 605, as shown by the arrow 685 in FIG. 6B. The invertible porous mesh may be locked in place as described above, using a lock (e.g., a ratcheting lock). Similarly, the occluder may also include a locking mechanism to releasably lock it in the expanded configuration.

In any of the apparatuses described herein the distal end of the apparatus may include a soft tip 678, which may be rounded, conical, pointed, etc. FIG. 6A also shows example dimensions; these dimensions are for illustration only and may be larger (including scaling up/down) or smaller.

FIGS. 6C-6D illustrate the operation of the apparatus of FIGS. 6A-6B when removing the invertible porous mesh. In FIG. 6C the mesh is removed by withdrawing the second elongate member 605 proximally. In this example the invertible porous mesh is removed by inverting and pulling into the first elongate member, but after the suction has been turned off (negative pressure off) and after removing the seal applied by the occluder 641, e.g., by sliding the occluder deployment member proximally, as shown in FIG. 6C. FIG. 6D shows the apparatus of FIG. 6A fully retracted. Thereafter the entire device may be removed from the tissue.

In variations of these apparatuses including an occluder, the occluder may be configured as a mechanical plug (e.g., an occluding seal portion). Although a bladder or balloon (inflated/deflated by hydraulic pressure) may be used, in some examples the occluder may instead by mechanically actuated, as shown in FIGS. 6A-6D. Mechanical activation may provide a direct relationship of expansion pressure to force, which may be intuitive and may be felt by the user operating the occluder directly. These mechanically actuated occluders may also be relatively quick to activate, as they do not require balloon filling or emptying.

The expansion of the invertible porous mesh (which may also be referred to as a drain mesh or simply drain) may produce a more distributed and lower stress vacuum load throughout the soft tissue (e.g., uterus in one example). Further, the device may be removed with much less trauma by inverting it into the apparatus as described above.

In any of these examples, the elongate members (both the first, e.g., outer, and second, e.g., inner) elongate members may be flexible, semi-ridged or rigid. For example, they elongate tubular members may be formed of polyurethane or silicone. These apparatuses may be configured to have reasonably high column force while retaining bending flexibility. The occluder may be formed as a plug, such as a braided plug as shown schematically in FIGS. 6A-6D. This mechanically-deployed seal or plug may be actuated by pushing or pulling to exert a mechanical force when shortening, without collapsing. In plugs formed from strands of knit, woven or braided material, the film covering the fibers may be highly flexible, e.g., having more than 1000% elongation, and may be very thin (e.g., ultra thin-walled, such as 0.1 mm or less, e.g. 0.9 mm or less, 0.8 mm or less, 0.7 mm or less, etc.).

In general, the invertible porous mesh may have a very high porosity when expanded (e.g., when shortened in length), and be soft so as to ovalize (as shown in FIG. 2C) by the action of the negative pressure on the tissue. The soft distal tip may be configured as an obturator, and may be formed, e.g., as a silicone bumper.

The rolling invertible porous mesh may distribute the negative pressure relatively evenly to a larger surface area. In particular, the area may be maximized as the invertible porous mesh may be expanded to have a larger coverage once inserted into the body region. The invertible porous mesh may therefore prevent tissue adhesions and/or damage when removed. In particular, examples of the invertible porous mesh in which the mesh is formed of one or more filaments (e.g., in some cases having a monofilament structure) may generally have a low surface area and may be removed by inverting and rolling inward to peel away, without shearing the tissue, unlike other surgical drains.

The invertible porous mesh may be formed into any appropriate shape, including biasing (pre-biasing) into any appropriate shape, such as, for example, a curved (e.g., "c" shape, banana shape, tapered, etc.).

Figure 7A:
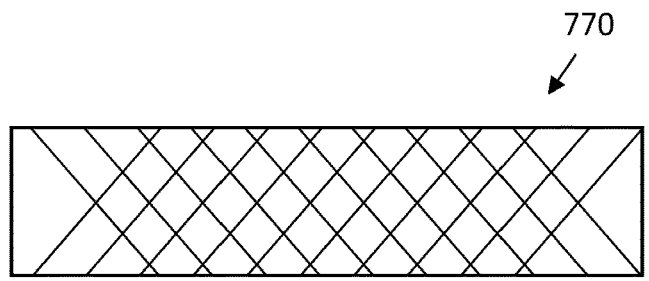
FIGS. 7A-7C illustrate the operation of an invertible porous mesh as described herein.
Figure 7B:
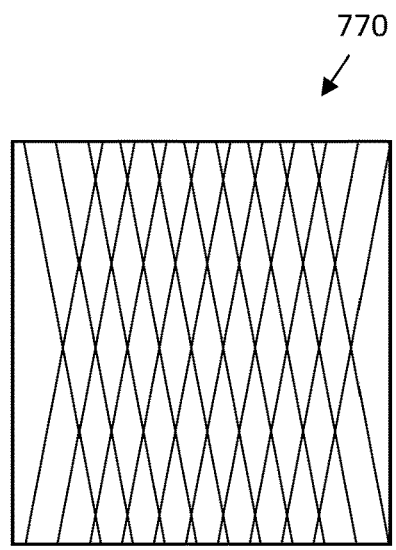
Figure 7C:
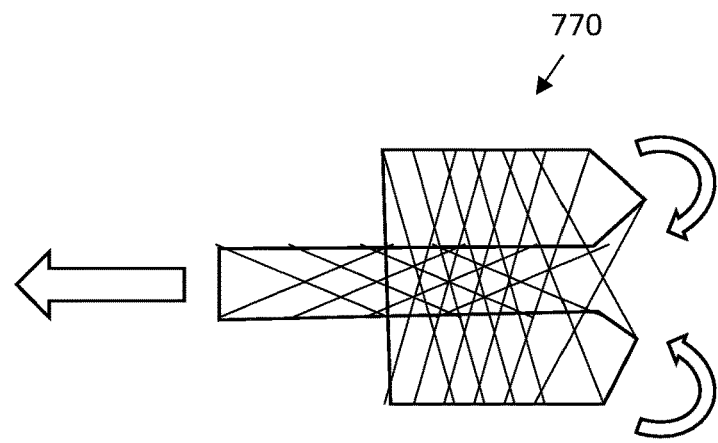

FIGS. 7A-7C illustrate the operation of one example of an invertible porous mesh 770. In FIG. 7A the invertible porous mesh is a shown at rest. In this example, the invertible porous mesh has a tubular shape; both ends are open. In some examples, one end may be closed (e.g., the distal end). When the invertible porous mesh is compressed longitudinally, as shown in FIG. 7B, the invertible porous mesh may form a jammed column that resists further compression; in this configuration the invertible porous mesh is maximally expanded. The invertible porous mesh may be radially compressed (see, e.g., FIG. 2C), within the tissue. The pores in both the at-rest form (FIG. 7A) and the expanded form (FIG. 7B) are large and extend over the entire invertible porous mesh, allowing fluid and material (e.g., blood, pus, etc. to enter the invertible porous mesh with little or no resistance. In FIG. 7B the filaments are packed together to form a stacked filament column, as shown. Pulling the end of the invertible porous mesh further may drive the tube to roll over and through itself, as shown in FIG. 7C, allowing the filaments to unstack inside of the stacked column, as shown by the arrows.

Figure 8A:
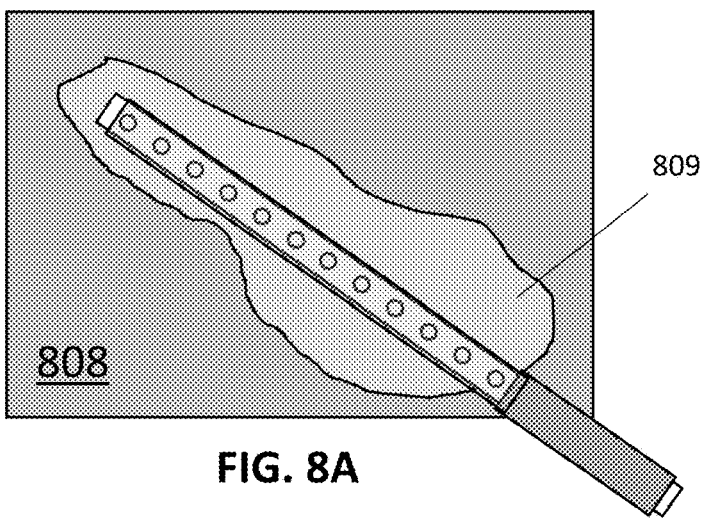
FIGS. 8A-8C illustrate an example of a rolling surgical drain apparatus within a body region (e.g. a surgical region or a wound).
Figure 8B:
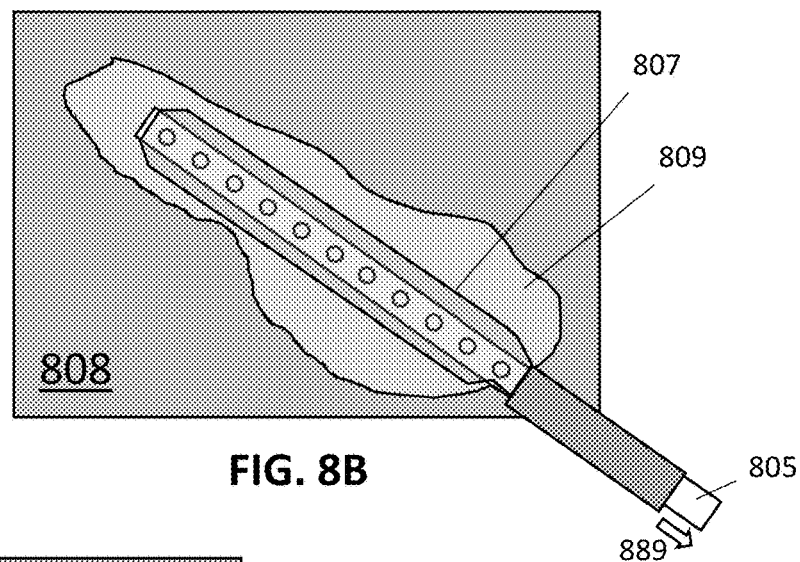
Figure 8C:
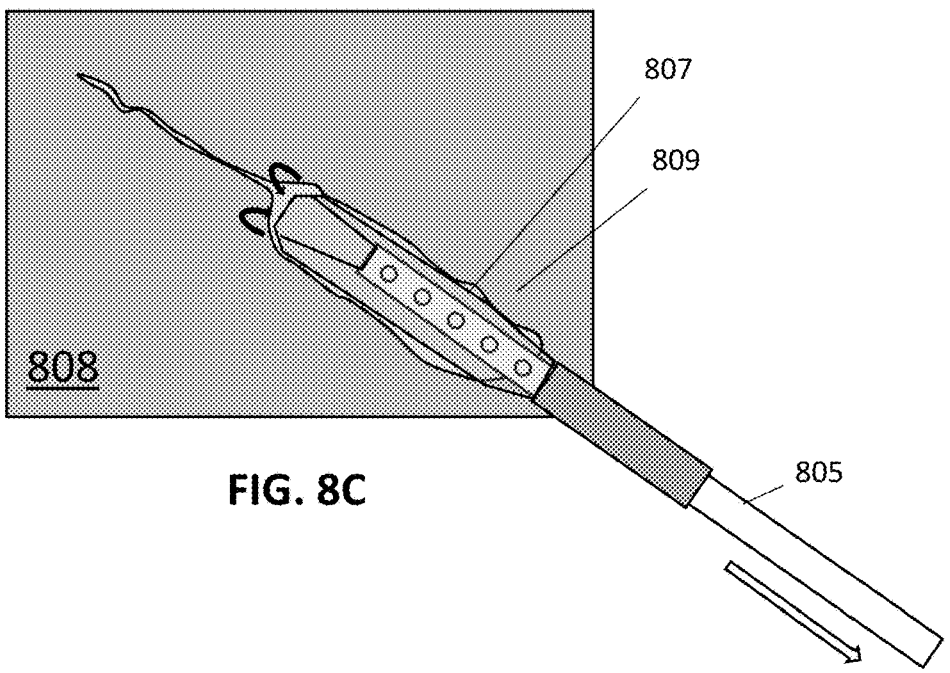

FIGS. 8A-8C illustrate one example of a method of operating an apparatus as described herein. In FIG. 8A the tissue 808 include a region of dead space 809, that may be filled with fluid, pus and/or debris. As described herein a rolling drain apparatus may be placed within the tissue, e.g., during or after surgery. For example, the apparatus (in this example, an apparatus similar to that shown in FIGS. 2A-2D) may be inserted into the dead space 809. As shown in FIG. 8B, the rolling drain portion (e.g., the invertible porous mesh 807) may be expanded once in position, e.g., by drawing the second elongate member (inner member) proximally, as shown by the arrow 889. Once in position, negative pressure may be applied through the distal vacuum openings, as described, and material may be drawn into the gap spaced within the invertible porous mesh. This may remove the fluid and substantially reduce the dead space volume, as shown in FIG. 8C. In this example, the invertible porous mesh 807 is being inverted (e.g., by pulling the second elongate member 805 proximally) and rolled into the elongate member to remove it from the tissue, so that the tissue may close behind it, as shown.

Figure 9A:
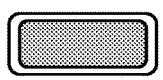
FIGS. 9A-9D illustrate examples of invertible porous mesh and supports (e.g., second elongate member) that may be used with any of the apparatuses described herein.
Figure 10A:
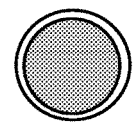
FIGS. 10A-10D illustrate examples of invertible porous mesh and supports (e.g., second elongate member) that may be used with any of the apparatuses described herein.
Figure 11A:
FIGS. 11A-11D illustrate examples of invertible porous mesh and supports (e.g., second elongate member) that may be used with any of the apparatuses described herein.
Figure 9B:
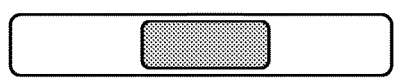
Figure 10B:
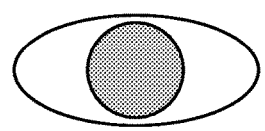
Figure 11B:
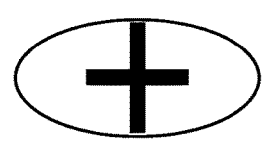
Figure 9C:
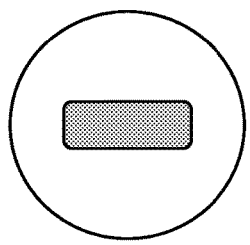
Figure 10C:
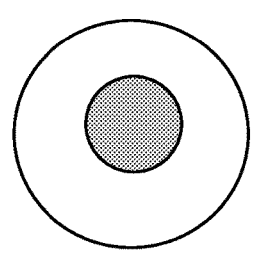
Figure 11C:
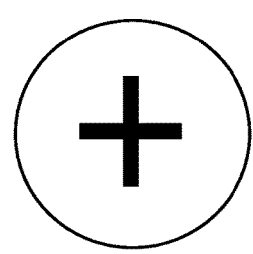
Figure 9D:
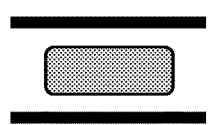
Figure 10D:
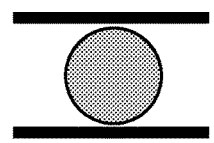
Figure 11D:
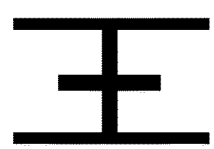

FIGS. 9A-9D, 10A-10D, and 11A-11D illustrate different examples of invertible porous meshes shown in a section view over a portion of a second elongate member. Different invertible porous meshes and different second elongate member profiles may be used. For example, in FIGS. 9A-9A both the second elongate member (which may be configured as hollow and may form part of the vacuum channel, not shown) and the invertible porous mesh may have a rectangular or "flat" configuration. In FIG. 9A the invertible porous mesh is shown hugging the outer surface of the second elongate member, as in the delivery configuration. FIG. 9B the invertible porous mesh is shown expanded outward radially from the second elongate member, as in the deployed configuration. FIGS. 9D and 9D show similar rectangular/flat second elongate member profiles, but the invertible porous mesh as a circular configuration (in FIG. 9C) or a sheet configuration (FIG. 9D). FIGS. 10A-10D show the second elongate member having a circular cross-section; in FIG. 10A the invertible porous mesh is shown in the delivery configuration (hugging the second elongate member). FIGS. 10B-10C show the invertible porous mesh in the deployed/expanded configuration. In FIG. 10B the invertible porous mesh is ovalized (either by pre-setting to this shape or by compressing of the tissue). In FIG. 10C the invertible porous mesh is fully expanded radially outward. FIG. 10D shows an example in which the invertible porous mesh includes a pair of fabric sheets. FIGS. 11A-11D show examples in which the second elongate member is formed as a "+" shape, forming four channel drains. FIG. 11A shows the section through the invertible porous mesh and second elongate member in the delivery configuration. FIGS. 11B-11C show the invertible porous mesh in the deployed/expanded configuration. In FIG. 11B the invertible porous mesh is ovalized (either by pre-setting to this shape or by compressing of the tissue). In FIG. 11C the invertible porous mesh is fully expanded radially outward. FIG. 11D shows an example in which the invertible porous mesh includes a pair of fabric sheets.

FIGS. 12A-12C illustrate another example of a rolling drain of a surgical drain system as described herein. In FIGS. 12A-12C the second (e.g., inner) elongate member is configured as the drain tube (e.g., vacuum channel) and extends from a proximal vacuum port (not shown) to the plurality of distal vacuum openings. Thus, the second elongate member may be a drain tube (or may include a drain tube) and may have any appropriate cross-sectional profile, including round, flat, may include channels, and/or may be flexible or stiff. In some examples the second elongate member may be trocar friendly.

In FIG. 12A, the second elongate member 1205 is attached at the distal end region to an invertible porous mesh 1207. The invertible porous mesh is also connected to the outer cuff 1201. The outer cuff may be part of (or may be coupled to) the first elongate member, as shown in FIGS. 1A-1E and 2A-2D, above. Thus, the invertible porous mesh may be expanded, as shown in FIG. 12B, by advancing the outer cuff 1201 distally, as shown in FIG. 12B. Finally, the invertible porous mesh may be inverted and drawn into itself for removal, from the body region, as shown in FIG. 12C.

Figure 13D:
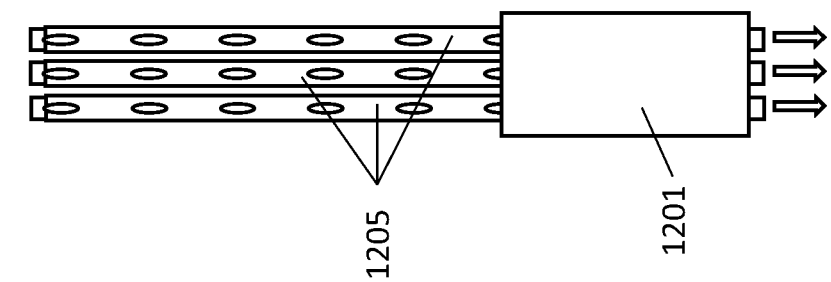
FIGS. 13A-13D show alternative examples of the negative pressure channel(s) and ports that may be used with any of the apparatuses described herein.
Figure 13C:
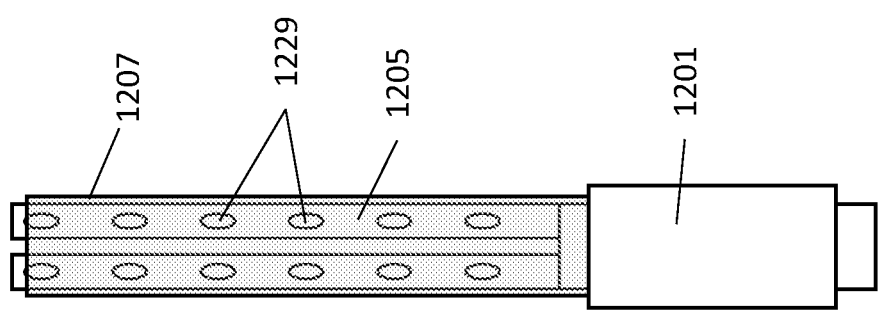
Figure 13B:
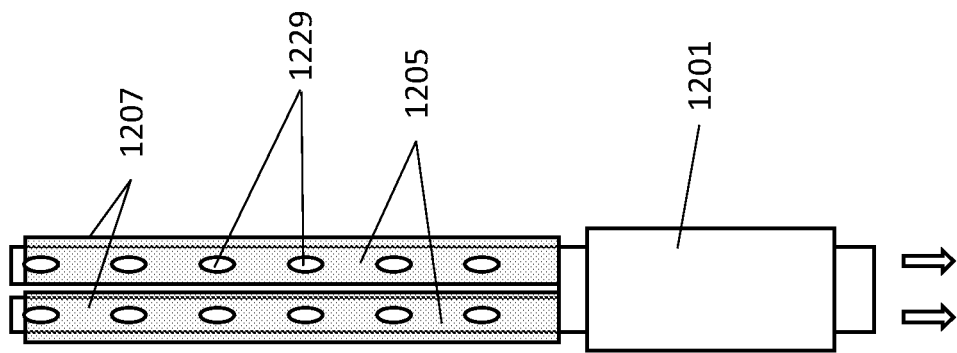
Figure 13A:
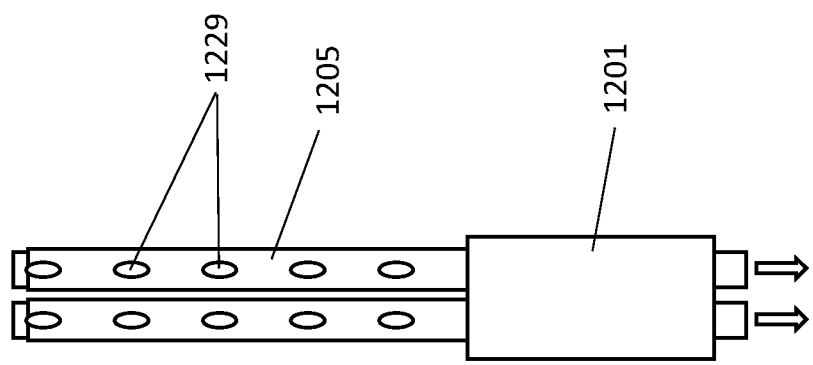

In some variations the "drain tube" formed by the second elongate member may include multiple channels, as shown in FIGS. 13A-13D. In FIG. 13A the distal end of the second elongate member forms a drain tube having multiple (e.g., 2, 3, 4, etc.) channels or branches, each including a plurality of openings 1229 forming distal vacuum openings. FIG. 13B shows the multiple-channel drain tube of FIG. 13A with two individual invertible porous mesh 1207 coverings each over a drain tube, as shown; the invertible porous mesh is attached at the distal ends of the drain tubes (e.g., the distal ends of the second elongate member) and the distal end of an outer cuff 1201, as shown. FIG. 13C shows the multiple-channel drain tube of FIG. 13A with a single invertible porous mesh 1207 covering the drain tube, as shown; the invertible porous mesh is attached at the distal ends of the drain tubes (e.g., the distal ends of the second elongate member) and the distal end of an outer cuff 1201, as shown. Finally, FIG. 13D shows a version including three drain tubes at the distal end of the second elongate member 1205.

Figure 14A:
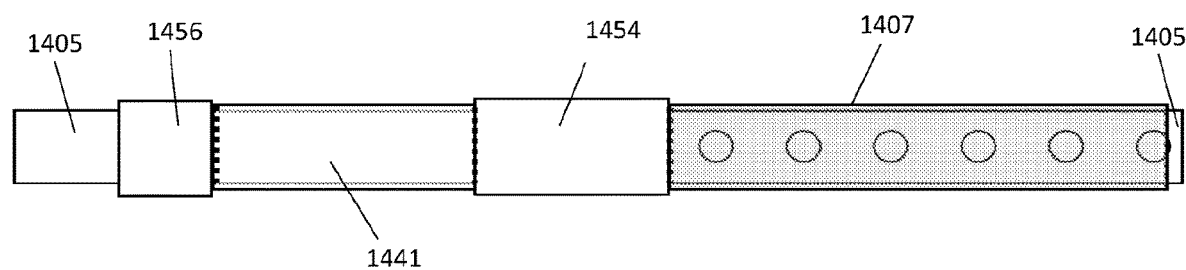
FIG. 14A-14B show another example of a sealing/anchoring region (e.g., an occluder region) that may be used with any of the apparatuses described herein.
Figure 14B:
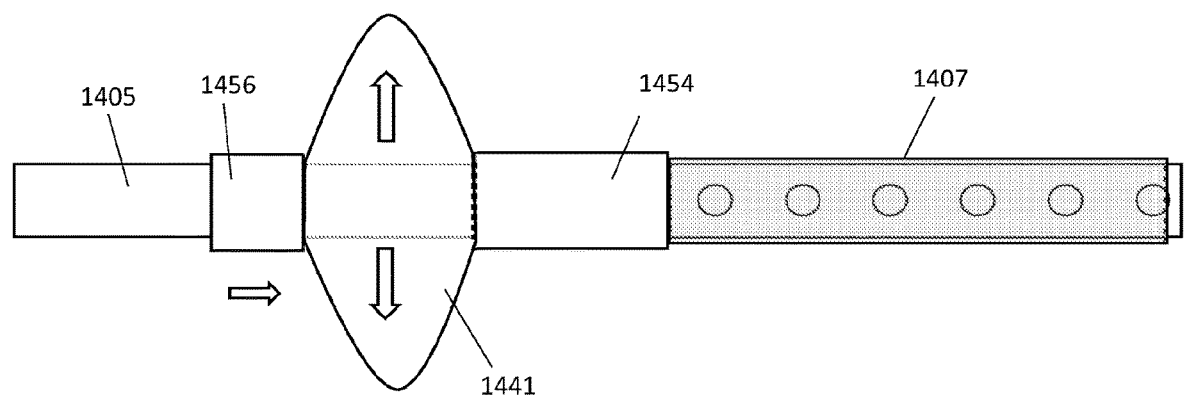

FIGS. 14A and 14B shows another example of an occluder portion of an apparatus, configure as a plug/anchor. In FIG. 14A the occluder (occluding seal portion) 1441 is configured as a plug or anchor that includes two layers: a braided tube (layer 1) and a film or membrane (layer 2). Radial pressure caused by compression of the braided tube expands and opens the anchor/plug 1441, as shown in FIG. 14B. In this example the proximal and distal ends of the occluding seal portion of the occluder are coupled to a first proximal cuff 1456 and a second distal cuff 1454, respectively. These cuffs are axially movable relative to a second (e.g., inner) elongate member 1405. The first cuff and/or the second cuff may be connected (or integral with) a first (e.g., outer) elongate member, in some examples. In FIGS. 14A-14B an invertible porous mesh 1407 is also coupled at one end to the second cuff 1454 and at the other end to the second elongate member, which may be configured as a drain similar to that shown in FIGS. 12A-12C and 13A-13D. In the examples shown in FIGS. 14A-14B each of the first cuff 1456 and the second cuff 1454 may be separately held or activated (moved axially) by one or more controls, such as a tendon or cable.

Figure 15A:
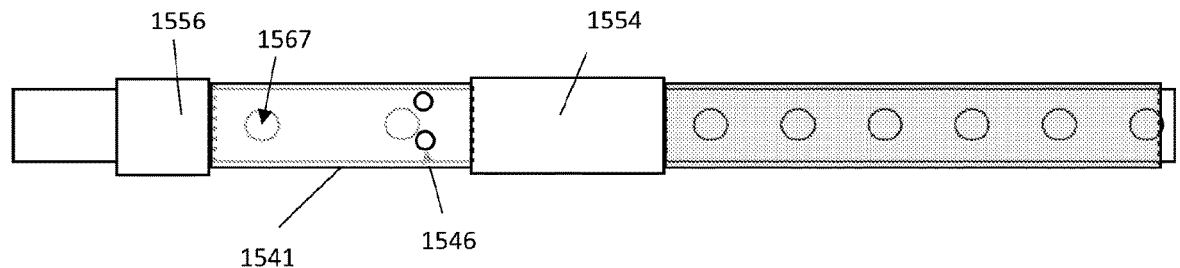
FIGS. 15A-15F illustrate operation of one example of an occluder region as described herein.
Figure 15B:
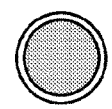
Figure 15C:
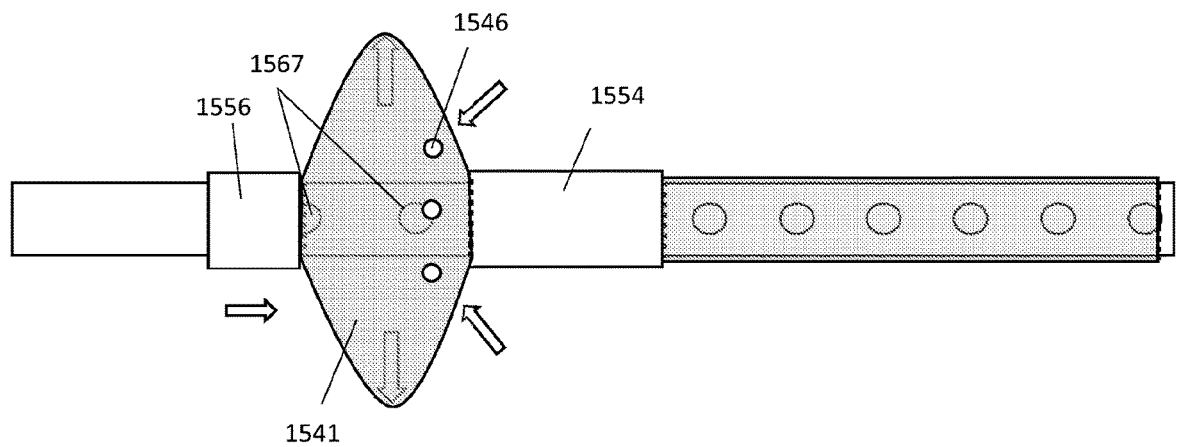
Figure 15D:
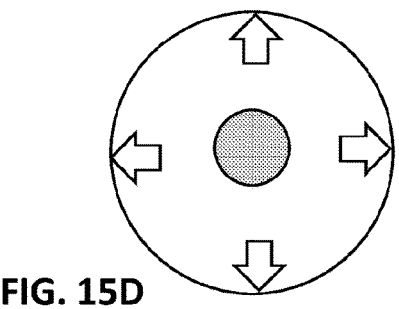

FIGS. 15A-15F illustrate the operation of a sealing plug/anchor (occluder) portion of an apparatus configured as a negative pressure seal. In FIG. 15A the distal portion of the apparatus includes an occluder (occluding seal portion) 1541. The occluding seal portion of the occluder includes optional openings/holes 1546. Similarly, the occluding seal portion may have one or more drain holes 1567 under the membrane forming the occluding seal portion. FIG. 15B shows an end view of the portion of the apparatus shown in FIG. 15A. FIGS. 15C and 15D shows the same apparatus as the occluder (occluding seal portion) 1541 is actuated, e.g., either manually or automatically. The occluder may be automatically actuated by applying negative pressure through the drain holes 1567; the negative pressure may draw tissue for sealing, which may I turn create an anchor (stopping any motion of the anchor) and sealing the tissue after removing excess fluid. Alternatively, the anchor/plug may be manually activated by pushing the first (e.g., proximal) cuff 1556 distally while holding the distal cuff 1554 locked in relative position (and/or by also moving the distal cuff proximally. FIG. 15D shows a section through the expanded occluder.

Figure 15E:
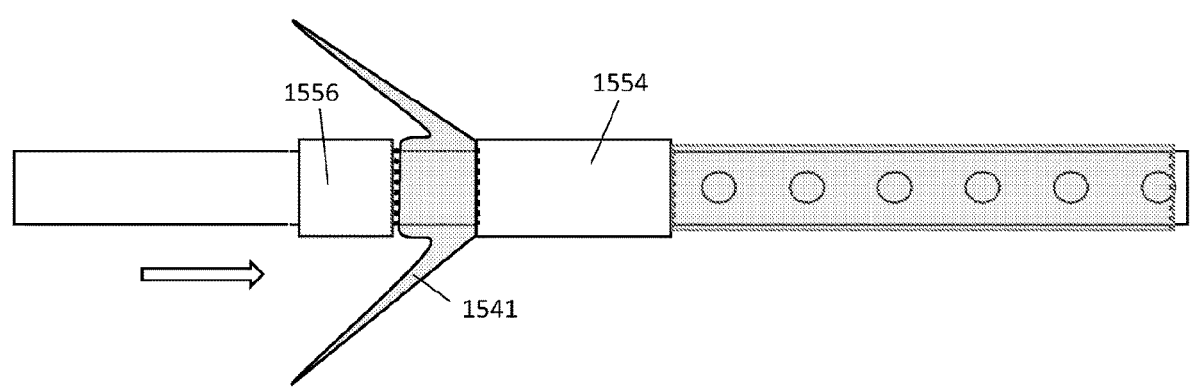
Figure 15F:
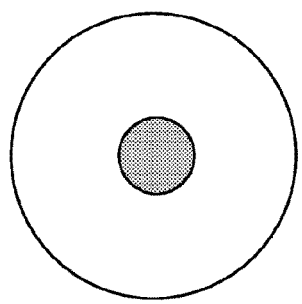

In some examples, the locking occluder may be configured to change conformation to lock the cuff in position, as shown in FIGS. 15E and 15F. In FIG. 15E the occluder region may be full anchored by driving the proximal cuff and distal cuff as closely together as possible, driving the confirmation of the occluder 1541 into a funnel shape, as shown. This funnel shape may act as a releasable and stable plug or seal.

In general, the apparatuses described herein may include a tip region which may be configured as an obturator. FIGS. 16A-16B illustrate an example of an apparatus including a soft obturator 1678 at the distal end that may pass with the rolled-up invertible porous mesh 1607 into the first elongate member. In FIG. 16A the apparatus is in the delivery configuration, with the invertible porous mesh pulled in tension so that it is held against the OD of the inner member. In FIG. 16B the invertible porous mesh has been deployed and is being rolled into itself and withdrawn into the apparatus. The soft distal tip (obturator) may be withdrawn into the first elongate member lumen along with the invertible porous mesh.

Alternatively or additionally, the distal end of the apparatus may be configured as a trocar 1708, as shown in FIG. 17. In this example, the apparatus includes the trocar formed of metal and/or polymer which may be used for trans-tissue tunneling.

In general, the apparatuses described herein may be used to drain a region of a body (e.g., a wound, a body cavity, etc.). For example, FIG. 18 schematically illustrates one example of a method of draining a body region, which may be performed using an apparatus as described herein. For example, in FIG. 18A, the method of draining a body region may include positioning a distal end of an invertible porous mesh into the body region 1801. The invertible porous mesh may be coupled at a first end to a distal end region of a first elongate member and at a second end to a distal end region of a second elongate member that is slidable disposed within a lumen of the first elongate member. The invertible porous mesh may then be expanded within the body region 1803, e.g., to form a gap at least partially around the second elongate member. Either before or after expanding the invertible porous mesh within the body region the method may include creating a seal to maintain a vacuum within the body region 1805. Negative pressure may then be applied through the invertible porous mesh 1807 (e.g., by applying negative pressure from one or more vacuum ports opening into the gap of the expanded invertible porous mesh). Once the body region is drained, and sufficient negative pressure has been applied, the invertible porous mesh may be removed (withdrawn) from the body region by inverting (e.g. by pulling the second elongate member to which the invertible porous mesh is attached, proximally), to invert the invertible porous mesh 1809. The invertible porous mesh may be withdrawn by inverting and pulling into the device body either while or after applying sufficient negative pressure to drain and potentially to cause the tissue to be pulled onto and/or against each other. The negative pressure may be maintained for a period of time (e.g., 10 minutes, 1 hour, 2 hours, 3 hours, 4 hours, 5 hours, 6 hours or more etc.) 1811.

Figure 18B:
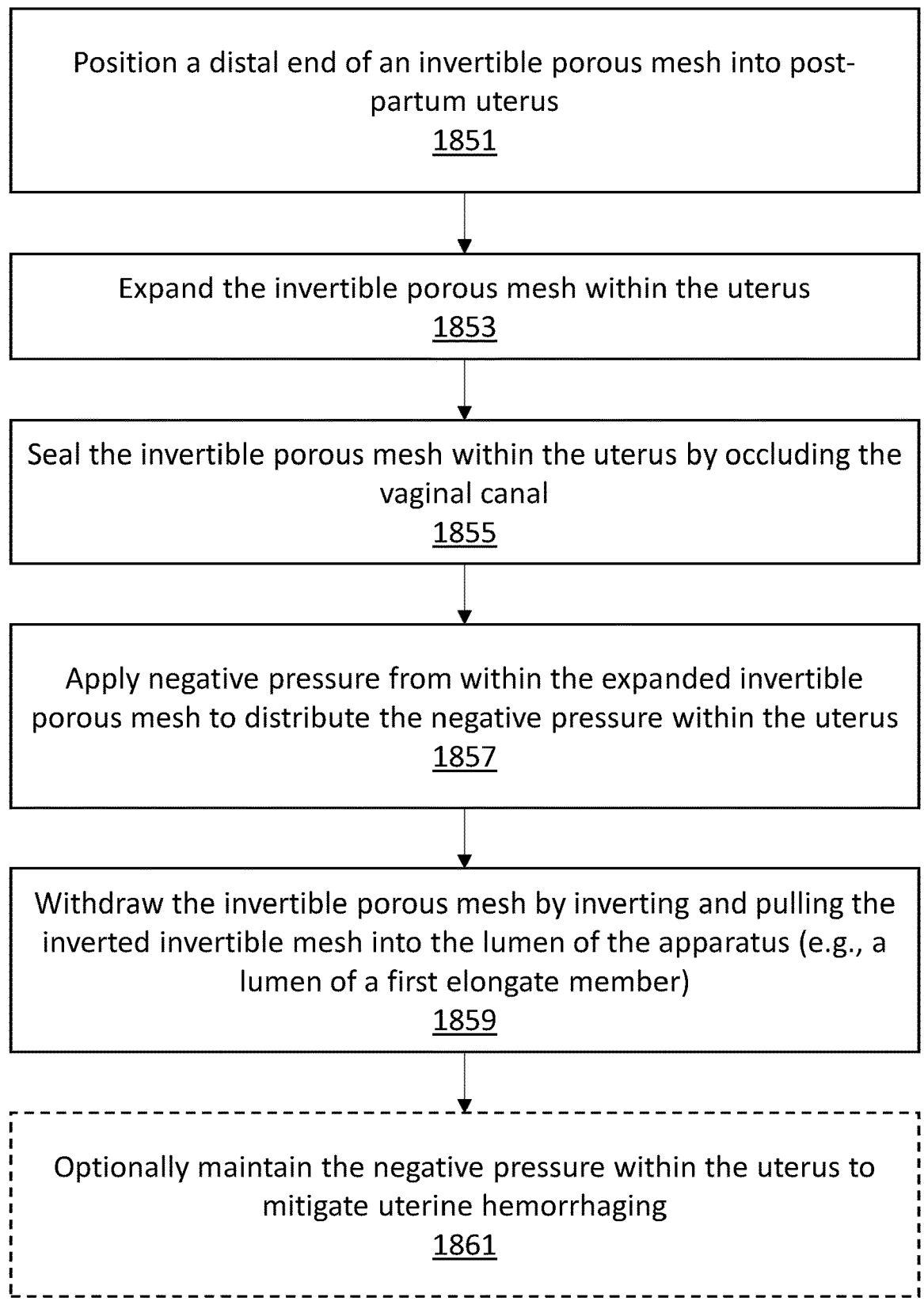
FIG. 18B schematically illustrates an example of a method of contracting a uterus to reduce hemorrhaging.

For example, the apparatuses and methods described herein may be used specifically to treat hemorrhaging, e.g., from the uterus following childbirth. FIG. 18B schematically illustrates one example of a method of contracting a uterus to reduce hemorrhaging, as described herein. In FIG. 18B, the method may include first positioning the distal end of an invertible porous mesh into the uterus 1851. The invertible porous mesh may be coupled at a first end to a distal end region of a first elongate member and at a second end to a distal end region of a second elongate member that is slidable disposed within a lumen of the first elongate member. The invertible porous mesh may then be expanded within the uterus 1853. This expansion may include transitioning from a deployment configuration to an expanded configuration, to form a gap at least partially around the second elongate member of the apparatus. Either before, during or after expanding the invertible mesh, a seal may be created, e.g., within the vaginal canal, to maintain a vacuum within the uterus 1855. Negative pressure may then be applied from within the space defined by the invertible porous mesh 1857, e.g., from one or more vacuum ports opening into the gap of the expanded invertible porous mesh. Thereafter, the second elongate member may be pulled proximally to invert the invertible porous mesh as the invertible porous mesh is pulled into the lumen of the first elongate member 1859. Finally, the method may include maintaining the negative pressure within the uterus 1861 to mitigate uterine hemorrhaging.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A surgical drain system, the system comprising:
a first elongate member having a first lumen;
a second elongate member that is slidably disposed in the first lumen;
an invertible porous mesh coupled at a first end to a distal end region of the first elongate member and at a second end to a distal end of the second elongate member, wherein the invertible porous mesh has an expanded configuration, in which the invertible porous mesh is extended distally out of the first elongate member, and a retracted configuration in which the invertible porous mesh is inverted and withdrawn into the first lumen, the invertible porous mesh having a pore size that is 1 mm or greater to allow fluid and clot material to pass easily and to distribute suction within a tissue region being treated, wherein the invertible porous mesh is configured to be withdrawn into the first elongate member after draining the tissue region; and
a vacuum channel extending around the second elongate member from a proximal vacuum port to a proximal end of the first elongate member so that the suction can be applied through the invertible porous mesh when it is extended distally of the second elongate member in the expanded configuration.

2. The system of claim 1, further comprising an occluder having an occluder lumen passing therethrough, wherein the occluder is configured to expand radially outward to seal a channel, further wherein the second elongate member is slidably disposed relative to the occluder lumen.

3. The system of claim 2, wherein the occluder is coupled to an outer surface of the first elongate member.

4. The system of claim 2, wherein the occluder comprises an expandable mesh to which a sealing membrane has been coupled.

5. The system of claim 2, wherein the occluder comprises a balloon.

6. The system of claim 2, wherein the occluder comprises a slidable proximal end configured to expand the occluder when driven distally and to collapse the occluder when driven proximally.

7. The system of claim 2, comprising an actuator configured to expand and contract the occluder.

8. The system of claim 1, wherein the first elongate member comprises a flexible and/or curved tube.

9. The system of claim 1, wherein the invertible porous mesh comprises a knitted, woven, or braided material.

10. The system of claim 1, wherein the invertible porous mesh comprises a non-woven material.

11. The system of claim 1, wherein the invertible porous mesh comprises a fabric.

12. The system of claim 1, wherein the invertible porous mesh comprises a braided polymeric monofilament having greater than 24 strands.

13. The system of claim 1, wherein the invertible porous mesh comprises a clot-promoting material.

14. The system of claim 1, further comprising one or more seals between the first elongate member and the second elongate member.

15. The system of claim 14, wherein the one or more seals comprises an O-ring.

16. The system of claim 1, further comprising one or more lock configured to lock a relative position of the first elongate member and the second elongate member.

17. A surgical drain system, the system comprising:
a first elongate member having a first lumen, wherein the first elongate member is flexible and/or curved;
a second elongate member that is slidably disposed in the first lumen;
an invertible porous mesh coupled at a first end to a distal end region of the first elongate member and at a second end to a distal end of the second elongate member, wherein the invertible porous mesh has an expanded configuration, in which the invertible porous mesh is extended distally out of the first elongate member, and a retracted configuration in which the invertible porous mesh is inverted and withdrawn into the first lumen, wherein the invertible porous mesh is configured to be withdrawn into the first elongate member after draining a tissue region;
a vacuum channel extending around the second elongate member from a proximal vacuum port to a proximal end of the first elongate member so that suction can be applied through the invertible porous mesh when the invertible porous mesh is in the expanded configuration, the invertible porous mesh having a pore size that is 1 mm or greater to allow fluid and clot material to pass easily, and to distribute the suction within a tissue region being treated; and
an occluder having an occluder lumen passing therethrough, wherein the occluder is configured to expand radially outward to form a seal against a channel, further wherein the second elongate member is slidably disposed relative to the occluder lumen.

18. The system of claim 17, wherein the occluder is coupled to an outer surface of the first elongate member.

19. The system of claim 17, wherein the occluder comprises an expandable mesh to which a sealing membrane has been coupled.

20. The system of claim 17, wherein the occluder comprises a balloon.

21. The system of claim 17, wherein the occluder comprises a slidable proximal end configured to expand the occluder when driven distally and to collapse the occluder when driven proximally.

22. The system of claim 17, further comprising a proximal actuator configured to expand and contract the occluder.

23. The system of claim 17, wherein the invertible porous mesh comprises a knitted, woven, or braided material.

24. The system of claim 17, wherein the invertible porous mesh comprises a non-woven material.

25. The system of claim 17, wherein the invertible porous mesh comprises a fabric.

26. The system of claim 17, wherein the invertible porous mesh comprises a braided polymeric monofilament having greater than 24 strands.

27. The system of claim 17, wherein the invertible porous mesh comprises a clot-promoting material.

28. The system of claim 17, further comprising one or more seals between the first elongate member and the second elongate member.

29. The system of claim 28, wherein the one or more seals comprises an O-ring.

30. The system of claim 17, further comprising one or more lock configured to lock a relative position of the first elongate member and the second elongate member.

* * * * *